(12) United States Patent
Wellisz et al.

(10) Patent No.: US 7,829,616 B2
(45) Date of Patent: Nov. 9, 2010

(54) RANDOM ETHYLENE OXIDE COPOLYMER AND NON-RANDOM ALKYLENE OXIDE(S) POLYMER

(75) Inventors: Tadeusz Wellisz, Los Angeles, CA (US); Timothy C. Fisher, Los Angeles, CA (US); Jonathan K. Armstrong, Los Angeles, CA (US); John Cambridge, Los Angeles, CA (US)

(73) Assignee: Syncera, Inc., Los Angeles, CA (US)

( * ) Notice: Subject to any disclaimer, the term of this patent is extended or adjusted under 35 U.S.C. 154(b) by 0 days.

(21) Appl. No.: 12/480,670

(22) Filed: Jun. 8, 2009

(65) Prior Publication Data
US 2009/0238758 A1   Sep. 24, 2009

Related U.S. Application Data

(63) Continuation of application No. 10/545,105, filed on Aug. 10, 2005, now Pat. No. 7,553,913.

(60) Provisional application No. 60/446,534, filed on Feb. 12, 2003.

(51) Int. Cl.
*A61F 2/02* (2006.01)
*C08K 3/22* (2006.01)
*C08L 23/06* (2006.01)
*C08L 71/02* (2006.01)

(52) U.S. Cl. .................. 524/415; 424/423; 424/434; 524/612; 525/187; 525/409; 604/19; 606/910

(58) Field of Classification Search .................. None
See application file for complete search history.

(56) References Cited

U.S. PATENT DOCUMENTS

| | | | |
|---|---|---|---|
| 3,634,305 A | 1/1972 | Johnson et al. | |
| 3,674,632 A | 7/1972 | Wennergren et al. | |
| 3,862,311 A | 1/1975 | Leeson | |
| 4,013,622 A | 3/1977 | DeJuneas et al. | |
| 4,027,676 A | 6/1977 | Mattei | |
| 4,038,388 A | 7/1977 | Cleaver | |
| 4,043,344 A | 8/1977 | Landi et al. | |
| 4,047,533 A | 9/1977 | Perciaccante et al. | |
| 4,201,216 A | 5/1980 | Mattei | |
| 4,407,953 A | 10/1983 | DeZeeuw et al. | |
| 4,439,420 A | 3/1984 | Mattei et al. | |
| 4,443,430 A | 4/1984 | Mattei et al. | |
| 4,470,416 A | 9/1984 | Kafrawy et al. | |
| RE32,208 E | 7/1986 | Mattei et al. | |
| 4,684,524 A | 8/1987 | Eckenhoff et al. | |
| 4,716,203 A | 12/1987 | Casey et al. | |
| 4,795,678 A | 1/1989 | Girgis | |
| 5,019,291 A | 5/1991 | Faulks | |
| 5,173,304 A | 12/1992 | Löhner et al. | |
| 5,283,067 A | 2/1994 | Geller et al. | |
| 5,286,300 A | 2/1994 | Hnatin et al. | |
| 5,308,623 A | 5/1994 | Fues et al. | |
| 5,330,768 A | 7/1994 | Park et al. | |
| 5,352,515 A | 10/1994 | Jarrett et al. | |
| 5,442,016 A | 8/1995 | Jarrett et al. | |
| 5,447,966 A | 9/1995 | Hermes et al. | |
| 5,487,897 A | 1/1996 | Polson et al. | |
| 5,503,558 A | 4/1996 | Clokie | |
| 5,520,923 A | 5/1996 | Tjia et al. | |
| 5,545,226 A | 8/1996 | Wingo et al. | |
| 5,641,502 A | 6/1997 | Skalla et al. | |
| 5,702,695 A | 12/1997 | Clokie | |
| 5,795,584 A | 8/1998 | Totakura et al. | |
| 5,817,321 A | 10/1998 | Alakhov et al. | |
| 5,840,319 A | 11/1998 | Alakhov et al. | |
| 5,840,338 A | 11/1998 | Roos et al. | |
| 5,912,228 A | 6/1999 | Lambert | |
| 5,939,485 A | 8/1999 | Bromberg et al. | |
| 6,060,518 A | 5/2000 | Kabanov et al. | |

(Continued)

FOREIGN PATENT DOCUMENTS

| CA | 2063278 | 6/1992 |
|---|---|---|
| CA | 1317100 | 5/1993 |
| DE | 2546371 | 4/1977 |
| DE | 3224784 | 1/1984 |

(Continued)

OTHER PUBLICATIONS

BASF Catalog, see especially Pluronic products, p. 34 (1997).

(Continued)

*Primary Examiner*—Robert Sellers
(74) *Attorney, Agent, or Firm*—Nixon & Vanderhye, P.C.

(57) ABSTRACT

A polymeric material comprised of (i) at least one random copolymer comprised of ethylene oxide and one or more other alkylene oxide(s) and (ii) at least one non-random polymer comprised of one or more poly(alkylene oxide)s has been discovered. Preferably, it is a polymer alloy. Alkylene oxide homopolymers or block copolymers may be the non-random polymer. In a related discovery, an adhesive material can be made by suspending (a) particles in (b) a matrix of at least one poly(ethylene oxide) copolymer of ethylene oxide and propylene oxide, or a combination thereof. The handling characteristics may be adjusted for different utilities (e.g., from runny oil to hard wax). Applications include use as adhesive, cohesive, filler, lubricant, surfactant, or any combination thereof. In particular, the hard materials may be used for cleaning or waxing.

36 Claims, 5 Drawing Sheets

U.S. PATENT DOCUMENTS

Figure 1A:
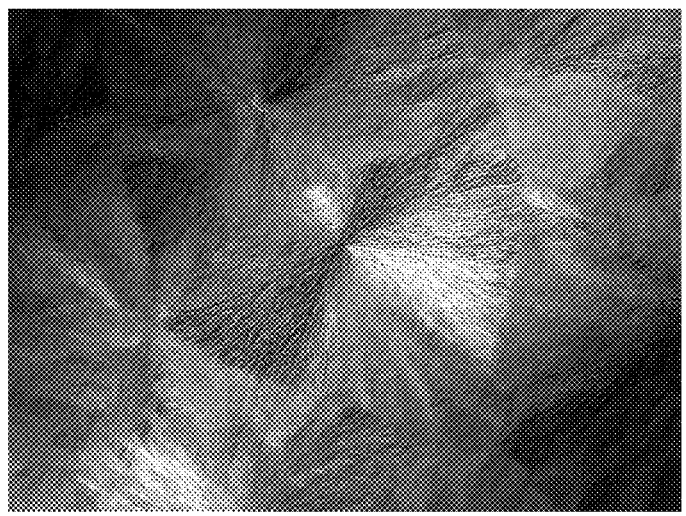

| | | | |
|---|---|---|---|
| 6,143,037 | A | 11/2000 | Goldstein et al. |
| 6,143,276 | A | 11/2000 | Unger |
| 6,265,016 | B1 | 7/2001 | Hostettler et al. |
| 6,296,607 | B1 | 10/2001 | Milbocker |
| 6,306,418 | B1 | 10/2001 | Bley |
| 6,309,659 | B1 | 10/2001 | Clokie |
| 6,328,990 | B1 | 12/2001 | Ducheyne et al. |
| 6,331,289 | B1 | 12/2001 | Klaveness et al. |
| 6,334,891 | B1 | 1/2002 | Constantz et al. |
| 6,376,588 | B1 | 4/2002 | Nieh |
| 6,406,498 | B1 | 6/2002 | Törmälä et al. |
| 6,417,247 | B1 | 7/2002 | Armstrong et al. |
| 6,432,437 | B1 | 8/2002 | Hubbard |
| 6,437,018 | B1 | 8/2002 | Gertzman et al. |
| 6,454,811 | B1 | 9/2002 | Sherwood et al. |
| 6,461,631 | B1 | 10/2002 | Dunn et al. |
| 6,685,956 | B2 | 2/2004 | Chu et al. |
| 6,762,339 | B1 | 7/2004 | Klun et al. |
| 6,770,688 | B1 | 8/2004 | Miyamoto |
| 7,553,913 | B2 | 6/2009 | Wellisz et al. |
| 2002/0025340 | A1 | 2/2002 | Dyer |
| 2002/0049363 | A1 | 4/2002 | Milbocker |
| 2002/0173213 | A1 | 11/2002 | Chu et al. |
| 2003/0082235 | A1 | 5/2003 | Cohn et al. |
| 2003/0095945 | A1 | 5/2003 | Levy et al. |
| 2003/0190336 | A1 | 10/2003 | Adams et al. |
| 2005/0008609 | A1 | 1/2005 | Cohn et al. |
| 2005/0069573 | A1 | 3/2005 | Cohn et al. |
| 2005/0165128 | A1 | 7/2005 | Cohn et al. |
| 2005/0215748 | A1 | 9/2005 | Milbocker |
| 2005/0282997 | A1 | 12/2005 | Ward et al. |
| 2006/0100370 | A1 | 5/2006 | Wellisz et al. |
| 2006/0140904 | A1 | 6/2006 | Wellisz et al. |

FOREIGN PATENT DOCUMENTS

| | | |
|---|---|---|
| EP | 0537891 | 8/1992 |
| EP | 0562612 | 9/1993 |
| EP | 0884052 | 12/1998 |
| EP | 1669093 | 6/2006 |
| FR | 2859988 | 3/2005 |
| JP | 55-147597 | 11/1980 |
| JP | 2-004854 | 1/1990 |
| JP | 5-214237 | 8/1993 |
| JP | 07-179804 | 12/1993 |
| JP | 2000-516246 | 12/2000 |
| JP | 2003-277800 | 10/2003 |
| WO | 88/01878 | 3/1988 |
| WO | 98/07434 | 2/1998 |
| WO | 99/08514 | 2/1999 |
| WO | 01/32101 | 5/2001 |
| WO | 2004/071451 A2 | 8/2004 |
| WO | 2004/071451 A3 | 8/2004 |
| WO | 2004/071452 A2 | 8/2004 |
| WO | 2004/071452 A3 | 8/2004 |

OTHER PUBLICATIONS

Bots et al. "Polyethylene oxide and 9003-11-6 for polyethylene oxide-polypropylene oxide" HCALPUS Accession No. 1987:9338 7:5 Registry No. 25322-68-3, 1986.

Byrd et al. Augmentation of the craniofacial skeleton with porous hydroxyapatite granules Plast. Reconstr. Surg. 91:15-22 (1993).

"Definitions of terms related to polymer blends, composites and multiphase polymeric materials" International Union of Pure and Applied Chemistry, pp. 1-29 (Oct. 2002).

Ersek et al. "Bioplastique: A new textured copolymer microparticle promises permanence in soft-tissue augmentation" Bioplast. 87:693-702 (1991).

Ersek et al. "Chin augmentation using minimally invasive technique and bioplastique" Plast. Reconstr. Surg. 95:985-992 (1995).

Fowler et al. "Evaluation of pluronic polyols as carriers for grafting materials: Study in rat calvaria defects" J. Periodontol. 73:191-197 (2002).

Insect Cell Culture Technical Information, Sigma Catalog, pp. 1469 and 1539 (1993).

Kabanov et al. "Pluronic block copolymers as novel polymer therapeutics for drug and gene delivery" J. Controlled Release 82:189-212 (Aug. 2002).

Lilla et al. "The long-term effects of hard alloplastic implants when put on bone" Plast. Reconstr. Surg. 58:14-18 (1976).

Rosen et al. "The biologic behavior of hydroxyapatite implanted into the maxillofacial skeleton" Plast. Reconstr. Surg. 85:718-723 (1990).

Schmitt et al. "Bone morphogenetic proteins: An update on basic biology and clinical relevance" J. Orthop. Res. 17:269-278 (1999).

Schmolka "A review of block polymer surfactants" J. American Oil Chem. Soc. 54:110-116 (1977).

Solheim "Growth factors in bone" Int'l Orthop. (SICOT) 22:410-416 (1998).

Technical data sheets for Pluronic L43, L61, 31R1 and 17R4, 2004, four pages, 2002.

Yaremchuk et al. "Implantable materials in facial aesthetic and reconstructive surgery: Biocompatibility and clinical applications" J. Craniofacial Surg. 7:473-486 (1996).

Wang et al. "A new, pluronic-based, bone hemostatic agent that does not impair osteogenesis" Neurosurgery 49:962-968 (2001).

Wellisz et al. "The effects of alloplastic implant onlays on bone in the rabbit mandible" Plast. Reconstr. Sur. 96:957-963 (1995).

Wellisz et al. "Characteristics of the tissue response to medpor porous polyethylene implants in the human facial skeleton" J. Long-Term Effects of Med. Implants 3:223-235 (1993).

Wellisz et al. "Ostene, a new water-soluble bone hemostasis agent" J. Craniofac. Surg. 17:420-425 (May 2006).

Wellisz et al. "The effects of a soluble polymer and bone wax on sternal healing in an animal model" Ann. Thorac. Surg. 85:1776-1780 (May 2008).

RANDOM ETHYLENE OXIDE COPOLYMER AND NON-RANDOM ALKYLENE OXIDE(S) POLYMER

CROSS-REFERENCE TO RELATED APPLICATIONS

This application is a divisional of application Ser. No. 10/545,105, filed Aug. 10, 2005, now U.S. Pat. No. 7,553,913; which claims priority benefit of provisional Application No. 60/446,534, filed Feb. 12, 2003; which are incorporated herein by reference. This is also related to Application No. PCT/US2004/004174, filed on Feb. 12, 2004; which is also incorporated by reference.

FIELD OF THE INVENTION

The invention relates to a composition comprised of (i) at least one random copolymer comprised of ethylene oxide and other alkylene oxide(s) and (ii) at least one non-random polymer comprised of one or more poly-(alkylene oxide)s (e.g., homopolymers and/or block copolymers).

BACKGROUND OF THE INVENTION

In the medical and surgical fields, there has been an unmet need for compositions with handling characteristics that range from a viscous oil to a hard wax. Desirable compositions would have one or more of the following properties: biocompatibility, non-metabolizable under physiological conditions, low toxicity and corrosiveness, readily eliminated from the body in unmodified form, easy and inexpensive to manufacture and store, long lived, and variable viscosity and hardness. Preferably, such compositions would be resorbed and readily eliminated by the body after they had served their intended purpose.

Such compositions would have a wide range of uses. For uses in the surgical field, compositions which have handling characteristics resembling a hard, adherent wax could be useful as a hemostatic agent that could be used to prevent bleeding from the surfaces of bones. Compositions with oily, greasy, or waxy characteristics (in ascending degrees of hardness) can be used as lubricants of surgical instruments and implants. Applications would include use as a carrier or excipient for particulate implantable materials, bioactive agents, and other pharmaceutical agents. The compositions are also suitable as a matrix for particulate material, adhesive/cohesive, filler, and/or lubricant; they may also be used as dispersing or suspending agents, emulsifiers, extenders, thickeners, and/or bodying agents for compositions, in particular for cosmetic and pharmaceutical formulations.

Until our discovery, there were no biocompatible, substantially non-toxic, water-soluble compositions available with handling characteristics that range from a grease to a wax over a temperature range from about 25° C. to about 37° C. for medical and surgical applications, which can be formulated to be substantially free of water (e.g., less than about 5% or about 1% water). All previously known water-soluble compositions with such handling characteristics and intended for medical or surgical applications contained water in their formulation.

Currently, the medical and surgical need for the appropriate formulations is being met in a number of different and less than acceptable ways. Most have the problem of either not being completely biocompatible or not having handling characteristics that are well suited for their intended application. Beeswax, commonly used as a bone hemostatic agent, is non-resorbable, interferes with bone healing, and causes inflammatory reactions. Compounds derived from biological sources, such as collagen, have the potential to cause immune reactions and may even have the potential to spread infectious agents. Many compounds in use fall into the category of hydrogels. Hydrogels consist of a three dimensional network of hydrophilic polymer chains in an aqueous medium that are cross-linked through either chemical or physical bonding. Theoretically, at least, the network is infinite and the polymer chains are effectively a single molecule. By definition hydrogels contain at least 10% water by total weight (or volume); but more commonly contain 10 to 50 times more water than polymer (w/w/ or w/v). Hydrogels in general do not have ideal physical characteristics for a material that needs to be handled and manipulated into position. They are typically elastic but not plastic, lacking malleability and ductility, and are often labile when exposed to compressive, tensile or shearing forces, leading to irreversible fracturing or tearing of the material. The water within hydrogels also may affect the lifetime of bioactive agents. Hydrocarbon compounds, either petroleum based (e.g., paraffin, petrolatum) or from other sources such as beeswax or plant-derived waxes, have the appropriate handling characteristics, but are not water soluble. Silicon oils and silicon gels are neither biologically inert nor water soluble. Thus, suitable polymers for therapeutic use remain to be discovered.

In the fields of surgery and dentistry, there is a need for an implantable material that contains a particulate component that can serve as a framework for tissue ingrowth. The particulate component can be selected from a broad range of natural and synthetic implantable substances, including but not limited to native autogenous bone or cartilage, bone or cartilage from other sources that is either grafted directly or after processing, collagen, hydroxyapatite, polymethylmethacrylate (PMMA), polytetrofluoroethylene (PTFE), polyethylene, and dimethylpolysiloxane.

The performance of particulate implants is markedly improved by the addition of a matrix to temporarily adhere the particles to one another and to form a putty that serves to improve the handling characteristics and acts as a delivery system. The majority of matrices in use or disclosed in the prior art are aqueous solutions or hydrogels including collagen, glycerol, polysaccharides, mucopolysaccharides, hyaluronic acid, plasdones, and polyvinylpyrrolidones (PVP).

Collagen, in the form of gelatin, has been used in ARTEPLAST® from Rofil Medical International. It is an injectable material comprised of microspheres of PMMA suspended in a gelatin solution. Following implantation, the gelatin is resorbed and replaced by native collagen. Another formulation, ARTECOLL® is a product currently available in Europe and Canada. It is comprised of smooth PMMA spheres, suspended in bovine collagen from a closed pharmaceutical herd at a concentration of 25% PMMA/75% collagen, by weight with 0.3% lidocaine. Because ARTECOLL® contains bovine collagen, testing for allergy to such collagen is recommended. Bovine collagen carries the risk of an immunogenic reaction by the recipient patient. Recently, it has been found that a disease of cattle, bovine spongiform encephalopathy (BSE) is transmitted from bovine tissue to humans. Thus, bovine collagen carries a risk of disease transmission and is not a desirable matrix for allograft bone. Human collagen is free of these animal-based diseases. However, collagen absorbs slowly in the human body, particularly in a bony site with a low degree of vascularity.

Glycerol is used as a matrix for demineralized allograft bone in the form of a gel. For example, GRAFTON from Osteotech is a simple mixture of glycerol and lyophilized, demineralized bone powder (U.S. Pat. No. 5,073,373). GRAFTON works well to allow the surgeon to place the allograft bone at the site. But glycerol has a very low molecular weight (92 daltons) and is very soluble in water, the primary component of the blood which flows at the surgical site. Glycerol also experiences a marked reduction in viscosity when its temperature rises from room temperature (typically 22° C. in an operating room) to the patient's body temperature (typically 37° C.). This combination of high water solubility and reduced viscosity causes the allograft bone with a glycerol matrix to be runny and to flow away from the site almost immediately after placement. This prevents the proper retention of the allograft bone within the site as carefully placed by the surgeon. The use of the low molecular weight glycerol carrier also requires a high concentration of glycerol to be used to achieve the bulk viscosity. Glycerol and other low molecular weight organic solvents are also toxic and irritating to the surrounding tissues. U.S. Pat. No. 6,306,418 describes the use of glycerol as the matrix for TEFLON particles in the field of urology.

Surgical implantation of artificial sphincters has often been employed to treat patients suffering from urinary incontinence. The most common and widely used method to treat patients with urinary incontinence is periurethral injection of a composition commercially sold as POLYTEF, which is a paste comprising a 1:1 by weight mixture of glycerin matrix and TEFLON particles. After injection, however, the glycerin is readily dissipated into the body over a period of time and then metabolized or eliminated, leaving only the TEFLON particles. A drawback of such a paste is that the size of the particles is sufficiently small so as to allow them to migrate to other locations of the body such as the lungs, brain, etc. TEFLON particles have been known to induce tissue reaction and form TEFLON-induced granulomas in certain individuals. This tissue reaction to TEFLON also has caused concerns for the patient's health.

U.S. Pat. No. 4,191,747 discloses a bone defect treatment with denatured bone meal freed from fat and ground into powder. The bone meal is mixed with a polysaccharide in a solution of saline and applied to the bone defect site.

U.S. Pat. No. 5,290,558 discloses a flowable, demineralized bone powder composition using an osteogenic bone powder mixed with a low molecular weight polyhydroxy compound possessing from 2 carbons to about 18 carbons including a number of classes of different sugars such as monosaccharides, disaccharides, water-dispersible oligosaccharides, and polysaccharides.

U.S. Pat. No. 5,356,629 discloses making a rigid gel in the form of a bone cement to fill defects in bone by mixing biocompatible particles preferably PMMA coated with polyhydroxyethylmethacrylate in a matrix (e.g., hyaluronic acid) to obtain a molded semi-solid mass which can be suitably worked for implantation into bone. The hyaluronic acid can also be utilized in monomeric form or in polymeric form preferably having a molecular weight not greater than about one million daltons. It is noted that non-bioabsorbable but biocompatible particles can be derived from xenograft bone, homologous bone, autogenous bone, as well as other substances. The bioactive substance can also be an osteogenic agent such as demineralized bone powder, in addition to morselized cancellous bone, aspirated bone marrow, and other autogenous bone sources. This is a cement used for implantation of hip prosthesis.

Ersek et al. describe the clinical use of soft particles delivered as a biphasic hydrogel material (Plast. Reconstr. Surg. 95:985-992, 1995). The material comprises solid particles of dimethylpolysiloxane ranging in size from 100 micron to 600 micron suspended in a hydrogel of the plasdone family.

BIOPLASTIQUE® material from Uroplasty, a biphasic material, consists of solid silicone particles, ranging from 100 microns to 400 microns in size, suspended in PVP. But this material elicits a low-grade inflammatory response upon injection. In a rabbit model, the hydrogel matrix is reabsorbed by the body within 96 hours and eliminated in an intact form by the kidneys. The hydrogel matrix is replaced by fibrin and inflammatory cells. Fibroblasts are recruited into the area by 14 days and begin to replace the fibrin bed with a collagen matrix. The collagen encapsulates and localizes the silicone, and animal studies have not shown any evidence of foreign body migration. Deposition of collagen progresses, replacing the organic component of the material in a ratio slightly greater than 1:1. Connective tissue cells develop and replace about 30% of the matrix with host collagen fibrils. At 382 days, fibrosis was complete and each individual particle appeared to be encased in its own fibrous capsule. This material has the distinct disadvantage of using silicone, which may be of concern when evaluating long-term safety.

U.S. Pat. No. 5,641,502 discloses a material comprising (i) a polymer derived from hydroxyacids, tactones, carbonates, etheresters, anhydrides, orthoesters, and copolymers, terpolymers and/or blends thereof and blended with (ii) at least one surface active agent which is from 2% to 55% by weight block copolymer of polyoxyethylene and polyoxypropylene. Additional, a leaching agent from 0% to 70% by weight may be included in the blend to provide a porous microstructure.

Poloxamer-based thermoreversible hydrogels are being developed for use as a drug delivery system. The cooled poloxamer solution containing the drug is liquid at less than 10° C. It is easily administered to the desired location in the body and the drug-containing solution forms a hydrogel as it warms to 37° C. The solidified gel remains at the site, slowly releasing the drug by diffusion and/or gradual solubilization of the gel matrix. Such compositions are distinguished from our invention because they do not include a random copolymer component, and do not have the wide variety of utilities disclosed herein.

U.S. Pat. No. 6,281,195 discloses a poloxamer hydrogel matrix for the delivery of osteogenic proteins. In particular, poloxamer 407 (PLURONIC® F127) is used in the form of a hydrogel. But hydrogels have disadvantages if used as the matrix instead of the present composition.

Therefore, in the field of surgery, a biocompatible, substantially non-toxic composition with adhesive and cohesive properties is needed. Hemostasis is an example of an application of such a composition. Bone is a structure with a rich blood supply. Blood within bone typically circulates through a system of canals and within the bone marrow and, as such, hemostasis using traditional methods, such as an electrocautery, is ineffective. Traditionally, bone hemostasis is obtained by applying a formulation primarily composed of beeswax onto the cut surface of the bleeding bone. The beeswax adheres to the bone and serves to act as a tamponade of the canals and bone marrow space, eventually leading to the clotting of the blood. Unfortunately, beeswax is not cleared by the body and acts to interfere with bone healing and inflammatory reactions are known.

Provisional U.S. Appln. No. 60/162,347 discloses a water-soluble wax for use as a bone hemostasis agent whose handling characteristics aim to simulate those of beeswax. The application of alkylene oxide block copolymers over the bleeding sites of the bone for hemostasis was described. Advantages over prior art methods include the finding that bone growth was not inhibited, and the water-soluble composition was resorbed and excreted. The preferred material described is a 9:1 blend by weight of two block copolymers: poloxamer 235 (PLURONIC® P85) and poloxamer 238 (PLURONIC® F88). But a random copolymer component was neither taught nor suggested. Blending poloxamer 235 and poloxamer 238 requires a precise combination of ingredients and snap cooling to preserve the blend, which is not a readily static mixture, and obtain the desired mechanical properties.

The formulations of bone hemostasis agents in the prior art lack one or more of the following attributes: biocompatibility, superior handling characteristics, and easy manufacture and storage. In contrast, preferred embodiments of the invention provide a biocompatible, substantially non-toxic, stable (i.e., non-metabolizable and readily eliminated) composition with superior handling characteristics.

It is an objective of the invention to provide a composition with superior properties for medical and surgical applications. Biocompatibility, substantial non-toxicity, water solubility, desirable handling properties (e.g., hardness, ductility, malleability), emulsification, filling, slipperiness (e.g., lubrication), surface activity (e.g., surface activity), tackiness (e.g., adhesion, cohesion), and thickening are characteristics of particular interest. Further advantages of the invention are described.

SUMMARY OF THE INVENTION

The invention relates to compositions which may be used in medicine, surgery, dentistry, and various other commercial (i.e., non-medical) utilities. Processes for making and using this product and related products are provided.

A polymeric composition may be comprised of (i) at least one random copolymer comprised of ethylene oxide and one or more other alkylene oxide(s) and (ii) at least one non-random polymer comprised of one or more poly(alkylene oxide)s. The non-random polymer may be a homopolymer or a block copolymer of at least two poly(alkylene oxide)s. The composition may be a polymer alloy. The composition can be biocompatible, substantially non-toxic to living tissue, substantially non-metabolizable under physiological conditions, readily eliminated in unmodified form by the body, or any combination thereof. The composition can be formulated to be water soluble, but contain no water (i.e., substantially anhydrous except for minor amounts of absorbed water). The composition may have a consistency of a viscous oil to a hard wax (including a grease or paste). Water may be added prior to use or absorbed in the body, but it is preferred to formulate the composition as a flowable liquid with less than about 5% or 1% water before use in the body or further formulation. Generally, it is not considered a hydrogel, especially before use in the body or further formulation.

Choice of the other alkylene oxide(s), molecular mass, mass ratio, and procedures during manufacture can affect the compound's properties: e.g., hardness, adhesiveness, cohesiveness, ductility, malleability, and hardness. For example, "working" the composition may change its characteristics by homogenizing its internal structure. Handling characteristics may be similar when compared between ambient temperature (e.g., 20° C. to 25° C.) and body temperature (e.g., 37° C. or 40° C.).

Such products may be administered to the body (e.g., applied topically to the skin or other exposed tissue, depot or suppository, implanted or placed therein, ingested, injected). Biocompatibility and substantial non-toxicity are desirable properties for such applications.

Another composition may be made by suspending (a) particles in (b) a carrier comprised of (i) at least one random copolymer comprised of ethylene oxide and one or more other alkylene oxide(s) and (ii) at least one non-random polymer comprised of one or more poly(alkylene oxide)s. This material may be adhered to hard tissue (e.g., tooth, bone, cartilage) with minimal adverse reaction by the tissue, the matrix may be resorbed to leave behind a porous framework of solid particles, and tissue may grow within the pores. In a preferred embodiment, the composition is made by mixing at an about 1:3 mass ratio of poloxamer 188 with 22K random alkylene oxide copolymer (AOC) to form a soft wax.

A polymeric alloy composition may be made by blending (a) at least one random copolymer comprised of ethylene oxide and one or more other alkylene oxide(s) and (b) at least one non-random polymer comprised of one or more poly(alkylene oxide)s.

An objective of the invention is to provide carriers and excipients. They may take advantage of any one of the beneficial properties described herein to deliver a therapeutic (e.g., bioactive agent, device, instrument) in the body of a human or animal. For example, the excipient may act as a lubricant to assist the passage or placement of the therapeutic in the body or a part thereof.

A further objective is to provide for an oral composition to be used as an excipient or as a laxative. In like fashion, it is intended to provide a component for cosmetic and pharmaceutical formulations for topical application, particularly for uses in which drawing fluid away from the application site is desirable.

Another objective is to provide a waxy material for utilities such as lost wax casting and water-soluble crayons. The composition may be used as a cleanser or stain remover. Lubricants, either flowable liquid or solid, to ease passage and to decrease friction are provided.

Further aspects of the invention will be apparent to a person skilled in the art from the following detailed description and claims, and generalizations thereto. In particular, a reference to a "composition" in the context of this invention includes compositions containing only polymers (e.g., blend or alloy of random copolymer and non-random polymer) as well as compositions with non-polymeric additives (e.g., bioactive agents, medical/surgical devices, implants, instruments, solid or porous particles, therapeutic or non-therapeutic products, and combinations thereof).

BRIEF DESCRIPTIONS OF THE DRAWINGS

Figure 1B:
Figure 1C:
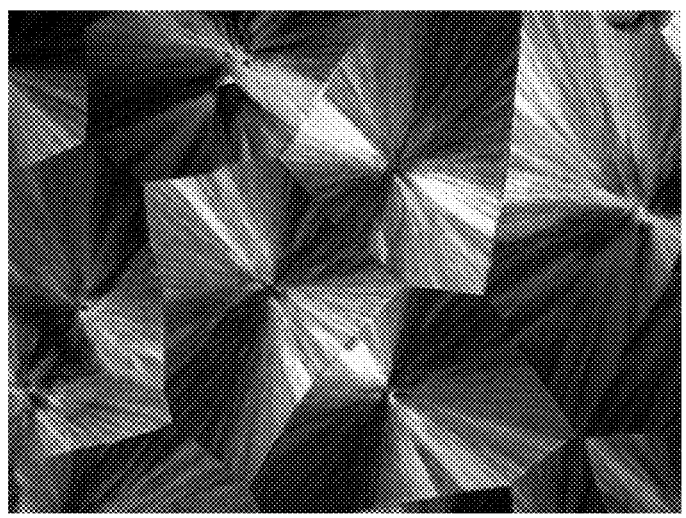
Figure 1D:
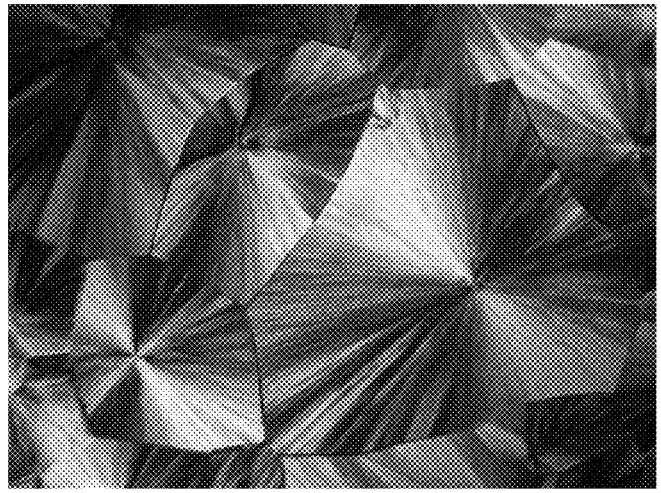
Figure 1E:
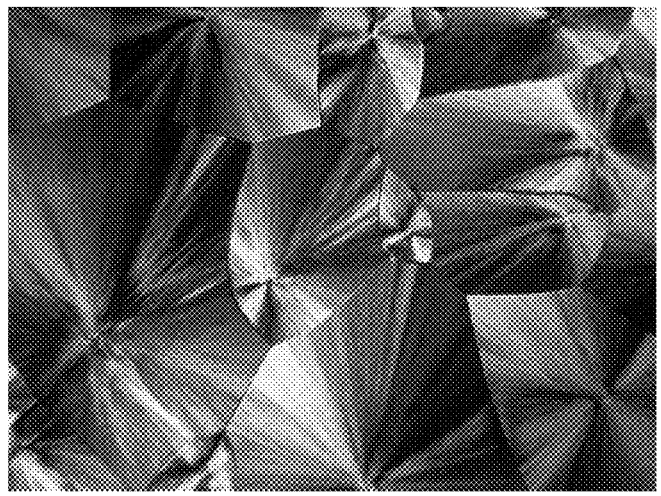
Figure 1F:
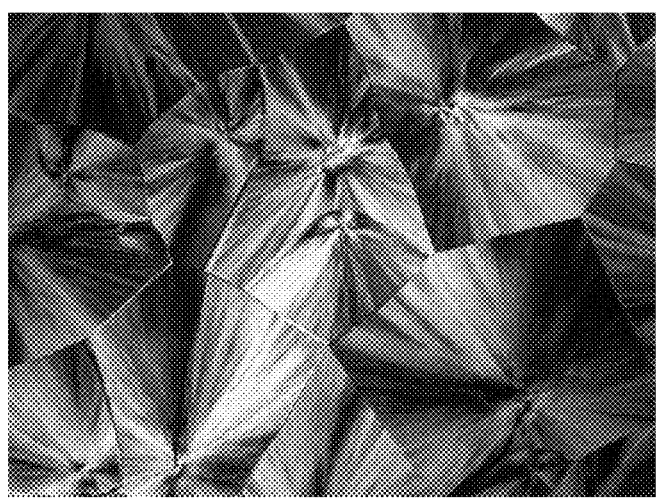
Figure 1G:
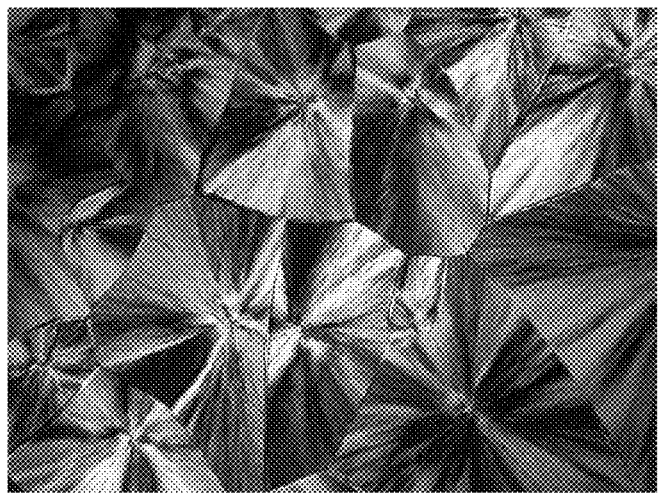
Figure 1H:
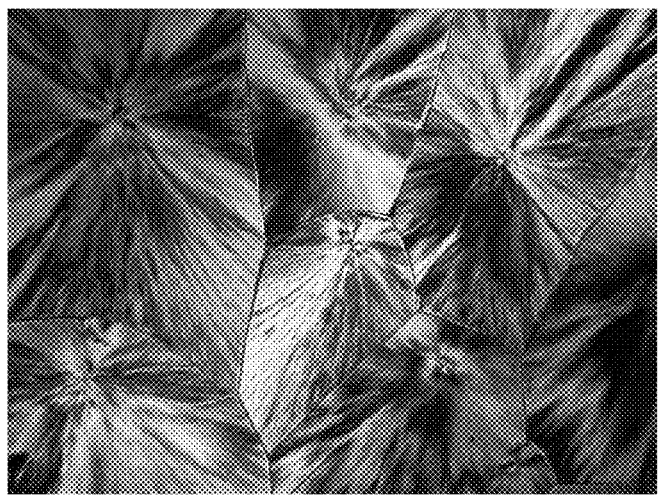
Figure 1I:
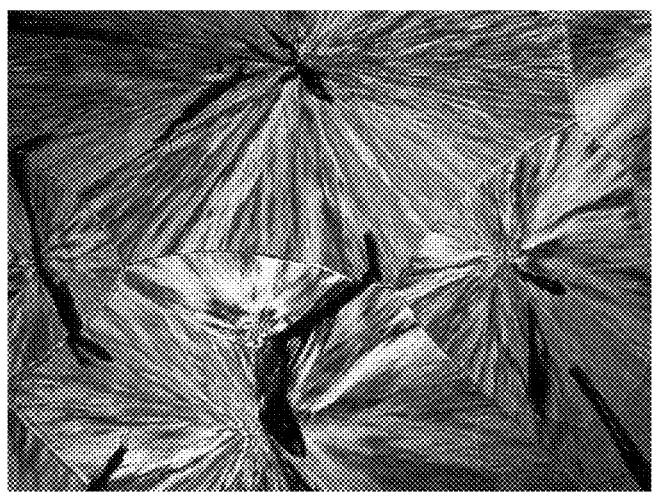
Figure 1J:
Figure 1K:
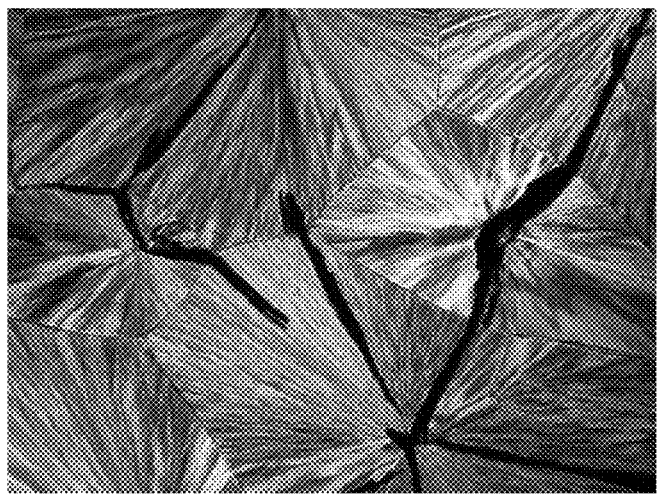
Figure 1L:
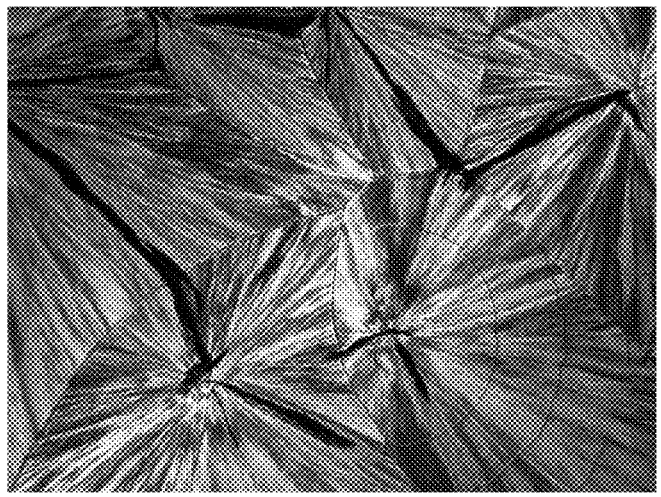

FIG. 1 illustrates crystals of compositions made with random AOC (about 22,000 g/mol; 50:50 mass ratio of ethylene oxide to propylene oxide) and block AOC, poloxamer 188 (PLURONIC® F68), in the following proportions of non-random polymer to random copolymer (F68:22K random AOC): (A) 2:98, (B) 5:95, (C) 10:90, (D) 20:80, (E) 30:70, (F) 40:50, (G) 50:50, (H) 60:40, (I) 70:30, (J) 80:20, (K) 90:10, or (L) 98:2. Single crystals were formed in all of the compositions, without gaps appearing between the crystals (i.e., a single component solid). This shows that they were all comprised of a compatible, homogeneous blend. Spherulite sizes did not appear to vary between mass ratios of 5:95 and 50:50. Above a mass ratio of 60:40, crystal size increased and spherulite rings and fractures became apparent. Fractures gave an opaque appearance to the solid sticks. They were clearly seen as black lines within and between the crystals for mass ratios between and 70:30 and 98:2.

Figure 2A:
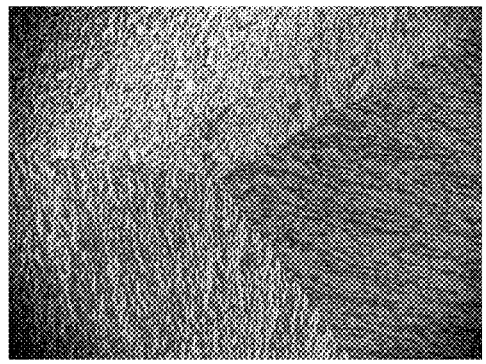
Figure 2D:
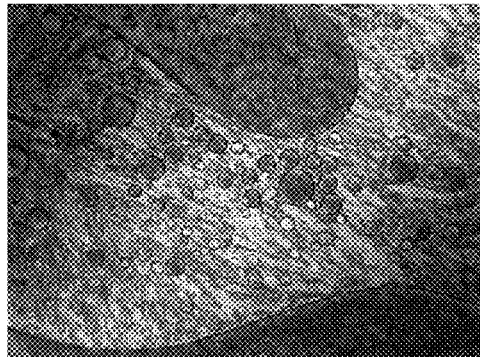
Figure 2B:
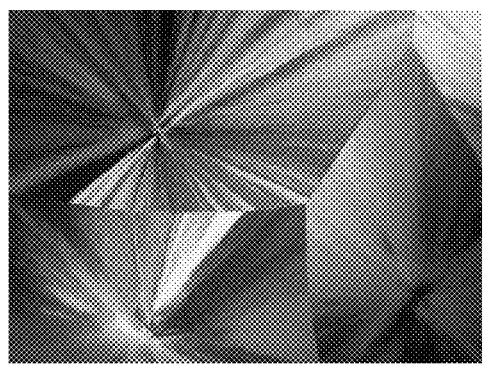
Figure 2E:
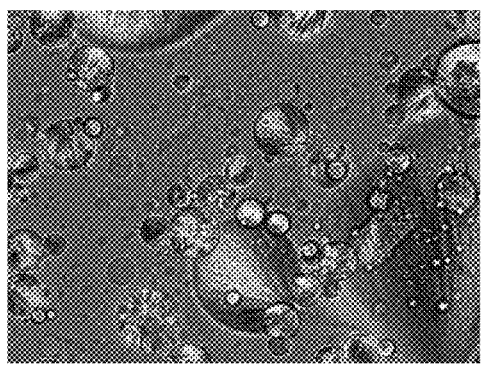
Figure 2C:
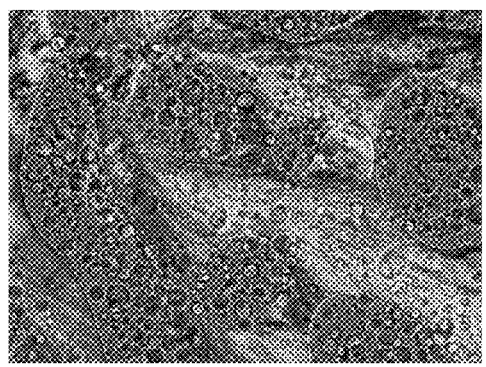

FIG. 2 illustrates crystals of compositions with the following random AOC and non-random polymer in equal mass proportions: (A) 3.5K PEO homopolymer and 12K random AOC, (B) poloxamer 188 and 12K random AOC, (C) 35K PEO homopolymer and 12K random AOC, (D) 2K PEO homopolymer and 3.9K random AOC, and (E) 7.5K PEO homopolymer and 3.9K random AOC, FIGS. 2A-2B are examples of compatible, miscible blends under the conditions and at the resolution used here. Spherulites without gaps between the crystals show that only a single phase was observed. FIGS. 2C-2E are examples of incompatible (immiscible) blends. There are clearly multiple phases observed, PEO in the melt phase forms discreet spherical crystalline droplets as it cools. FIG. 2D illustrates the presence of some compatible (fibrous) regions. Under the definition of AOC alloy used herein, FIGS. 2A-2B illustrate examples of polymer alloys but incompatible compositions are illustrated in FIGS. 2C-2E.

DESCRIPTION OF SPECIFIC EMBODIMENTS OF THE INVENTION

Those skilled in the art will appreciate that the compositions described here may be utilized for a wide variety of applications. The present invention provides for water soluble, biocompatible, substantially non-toxic, substantially non-metabolizable, and/or readily eliminated compositions. Compositions which are polymer alloys are preferred. A "polymer alloy" defined under the conditions described here is a macroscopically homogeneous composition of two or more different species of polymers which is comprised of compatible polymer blends and miscible polymer blends, but this definition excludes incompatible polymer blends. The specified attributes and handling characteristics of the composition can be designed as shown herein by appropriate selection of polymers, as well as their molecular masses and ratios.

The composition may be made by blending a polymeric material comprising (i) at least one random alkylene oxide copolymer (random AOC) and (ii) at least one non-random alkylene oxide polymer. The random AOC may be comprised of ethylene oxide and one or more alkylene oxide(s). The non-random polymer may be homopolymer (AOH) and/or copolymer (block AOC).

Poly(alkylene oxide)s (PAO) which are also known as polyoxyalkylenes (POA) are made by the polymerization of alkylene oxides (e.g., ethylene oxide, propylene oxide, butylene oxide). A homopolymer is formed only from one type of alkylene oxide while a copolymer is formed from two or more different alkylene oxides, known as alkylene oxide copolymers (AOC). Examples of the former are poly(ethylene oxide) (PEO), which is a polymer of ethylene oxide (EO), and poly(propylene oxide) (PPO), which is a polymer of propylene oxide (PO). Poly(ethylene oxide) is also commonly known as polyethylene glycol (PEG) or polyoxyethylene (POE). The molecular weight of such polymers is generally characterized as the average of a distribution of lengths (or repeat units). PEO is amphiphilic, extremely hydrophilic, water soluble, biocompatible, and substantially non-toxic and is produced commercially in a wide range of molecular weights (200 g/mol to 10 million g/mol). Low molecular weight forms of POE below 600 g/mol (i.e., oligomeric forms with less than 14 EO monomer units on average) are low-viscosity liquids at room temperature; PEO is a solid at 25° C. above 600 g/mol. PPO differs from PEO in that it is hydrophobic, generally insoluble in water except at low molecular weights (less than about 1 kg/mol), and is liquid at 25° C. even at high molecular weights (e.g., 6 kg/mol). The homopolymer may have a molecular mass of at least about 1 kg/mol, about 2 kg/mol, or about 5 kg/mol; the molecular mass may also be not more than about 10 kg/mol, about 20 kg/mol, or about 50 kg/mol. The compound may be further described by intermediate ranges using the aforementioned upper and lower limits.

In addition to the standard linear forms, branched or star forms of poly-(alkylene oxide)s are produced by initiating the polymerization reaction with a polyfunctional initiator with multiple hydroxyl-, amino-, or thiol-groups each of which can serve as a starting point for polymer chain growth. For example, the use of glycerol (three hydroxyl groups) as an initiator results in a three-armed branched polymer, while pentaerythritol results in a four-armed polymer. PEO molecules of this type are available commercially (e.g., the Sunbright™ series, NOF Corporation, Japan) with anywhere from three to more than one hundred arms. Conventionally, polymers of this type with 3 to 10 arms are termed "branched" while those with more than 10 arms are termed "star" polymers. "Comb" copolymers are similar to branched and star forms, but the initiator for comb copolymers is a polyfunctional polymer with multiple hydroxyl-, amino-, or thiol-groups spaced along the initiator backbone, each of which can serve as a staring point for polymer chain growth. "Graft" copolymers are made by the addition of pendant polymer chains along a polymer backbone that possesses unsaturated C=C bonds or pendant functional groups (e.g., hydroxyl) from which pendant chains can be added by using a reactive monofunctional polymer chain.

All poly(alkylene oxide)s contain, in addition to multiple alkylene oxide-derived repeat units, a single residue corresponding to the molecule used to initiate the polymer synthesis. For linear polymers, this may be an alkylene glycol corresponding to the alkylene oxide used for the synthesis (e.g., ethylene glycol and ethylene oxide, respectively) and thus the initiator-derived residue will be indistinguishable from the other repeat units in the polymer chain. But small molecules other than alkylene glycols are often used as initiators, examples include methanol or N-butanol (for linear polymers) and trimethylol propane, glycerol, and pentaerythritol (for branched polymers) or ethylene diamine. The mass of initiator relative to the mass of the final polymer chain is generally very small and can usually be neglected. Thus, the term poly(alkylene oxide) is used here in its customary sense, and includes both poly(alkylene oxide)s initiated with an alkylene glycol molecule and poly(alkylene oxide)s initiated with another small molecule.

Water-soluble poly(alkylene oxide)s are substantially non-toxic when applied to the skin or taken orally, and PEG and some poloxamers (e.g., F68 or poloxamer 188) have been evaluated for medical and surgical applications, and demonstrated to be suitable for parenteral use.

Random Alkylene Oxide Copolymer

Random AOC preferably has a molecular mass from about 1 kg/mol to about 1000 kg/mol (i.e., average molecular mass of a distribution of polymers). It may have a molecular mass of at least about 5 kg/mol, about 10 kg/mol, or about 20 kg/mol; the molecular mass may also be not more than about 25 kg/mol, about 50 kg/mol, or about 200 kg/mol. The mass ratio of ethylene oxide to the other alkylene oxide(s) preferably is from about 5:95 to about 95:5. It may have a mass ratio of at least about 10:90, about 25:75, or about 40:60; the mass ratio may also be not more than about 60:40, about 75:25, or about 90:10. The compound may be further described by intermediate ranges using the aforementioned upper and lower limits.

A preferred random AOC is a copolymer of ethylene oxide and $C_nH_{2n}O$, where n=3 to 6. In a particular embodiment, the molecular mass may be from about 15 kg/mol to about 30 kg/mol. Preferably, the molecular mass is at least about 20 kg/mol and/or not more than about 25 kg/mol and has a mass ratio of ethylene oxide to propylene oxide that is substantially equimolar.

In contrast to block AOC, a random copolymer of alkylene oxide(s) can be synthesized directly from an appropriate mixture of alkylene oxides, and thus the different alkylene oxide molecules are added to the polymer chain in a random sequence. The random AOC may be copolymer(s) of EO and PO. Random EO/PO copolymers have a certain combination of properties which distinguish them from EO and PO homopolymers and block AOC, and which make them uniquely useful as excipients for certain pharmaceutical applications. The most important of these is that they combine two of the desirable properties of PEO and PPO—i.e., they are liquids at room temperature and above over a wide range of molecular weights, but are water soluble. In contrast, except at very low molecular weights (less than 1000 g/mol), PPO is not water soluble and POE is a solid. Also, unlike most block copolymers, random AOC do not in the pure state self-associate to form structured domains or a crystalline structure (hence their liquid nature). Like all other PAO, they are soluble in selected organic solvents, able to solubilize many organic and inorganic substances including hydrophobic drugs that are poorly soluble in water, and have very low toxicity.

There is some evidence that small PEO molecules (600 g/mol or less) may be metabolized in vivo to produce oxalate, which is toxic. But larger PAO are known to be effectively inert and non-metabolizable in vivo, and are excreted unchanged. This provides a further advantage of the higher molecular weight random PAO liquids vs. liquid PEO.

A preferred embodiment uses a random alkylene oxide copolymer with a molecular weight of about 22 kg/mol (22K random AOC) and an EO:PO mass ratio of about 50:50. Such a compound is commercially available from BASF Corporation as PLURACOL® V-10 According to its manufacturer, V-10 was developed specifically for use in water-glycol fire-resistant hydraulic fluids and is additionally suitable as a water-soluble, cutting and grinding fluid and in various metal working applications. Furthermore, the manufacturer discloses that complete toxicity information on V-10 has not yet been fully developed and that the normal precautions exercised when handling any chemical should be used when working with V-10: e.g., eye protection should be used and prolonged contact with the skin should be avoided. Another preferred embodiment is a random alkylene oxide copolymer with a molecular weight of about 12 kg/mol (12K random AOC) and a mass ratio EO:PO of about 75:25.

Random AOC are produced by several manufacturers including BASF, Dow Chemical, and Sigma/Aldrich under the trade names PLURADOT®, PLURACOL®, SYNALOX® EPB, and EMKAROX® among others. They are available in a range of EO:PO ratios and molecular weights (e.g., 1000 to 22,000 g/mol) and in linear and branched geometries, and are commonly characterized by their viscosity rather than molecular weight. Dow Chemical provides a number of random AOC with molecular weights in the range of 1,500 to 4,900 including those with the following codes: EP 530, EP 1730, EP 435, EP 1660, 15-200, 112-2, UCON 50-HB-5100, and UCON 50-HB-660. Sigma/Aldrich provides a number of random AOC with molecular weights in the range of 2,500 to 12,000 including those with the following codes: 43,819-7, 43,820-0, 43,818-9, 40,918-9. Medical applications for PAO have been focused on block AOC. In contrast, the use of random AOC has almost exclusively been restricted to nonmedical applications, and their potential for providing medical benefits has been largely overlooked.

Block Alkylene Oxide Copolymer

Block AOC may be linear or branched, and preferably has a molecular mass from about 1 kg/mol to about 100 kg/mol (i.e., average molecular mass of a distribution of polymers). It may have a molecular mass of at least about 2 kg/mol, about 4 kg/mol, about 6 kg/mol, or about 10 kg/mol; the molecular mass may also be not more than about 10 kg/mol, about 15 kg/mol, about 20 kg/mol, or about 50 kg/mol. A preferred block AOC is a copolymer of ethylene oxide and $C_nH_{2n}O$, where n=3 to 6 (propylene oxide is preferred). The mass ratio of ethylene oxide to the other alkylene oxide(s) preferably is from about 5:95 to about 95:5. It may have a mass ratio of at least about 10:90, about 25:75, or about 40:60; the mass ratio may also be not more than about 60:40, about 75:25, or about 90:10. The compound may be further described by intermediate ranges using the aforementioned upper and lower limits. Preferred embodiments use a block alkylene oxide copolymer with (1) a molecular mass from about 6 kg/mol to 10 kg/mol and an EO:PO mass ratio from 60:40 to 90:10 or (2) a molecular mass from about 6 kg/mol to 10 kg/mol and an EO:PO mass ratio from 60:40 to 90:10.

Block copolymers are synthesized sequentially. First, a central block is commonly polymerized from one type of alkylene oxide (e.g., PO), then one or more outer blocks are added to the ends in a second polymerization step using another alkylene oxide (e.g., EO). Poloxamers (e.g., PLURONIC® copolymers from BASF) are linear A-B-A triblock copolymers of EO and PO having the general formula $(EO)_x(PO)_y(EO)_x$, where x, y are the average number of EO and PO monomer units in the block. A hydrophobe of the desired molecular weight is made by the controlled addition of propylene oxide to the two-hydroxyl groups of propylene glycol; ethylene oxide is then added to sandwich the hydrophobic block between hydrophilic blocks. The hydrophilic blocks constitute from 10% to 80% by weight of the final molecule. Poloxamers are available in a range of molecular weights from 1,100 to 15,000 g/mol and PO:EO ratios of 9:1 to 2:8. Meroxapols (e.g., PLURONIC® R from BASF) are linear triblock copolymers similar to poloxamers but with a reversed (B-A-B) structure and hence the general formula $(PO)_y(EO)_x(PO)_y$. A hydrophile of the desired molecular weight is made by the controlled addition of ethylene oxide to ethylene glycol; propylene oxide is then added to create hydrophobic blocks on the outsides of the central hydrophilic block. The physical properties of block copolymers range from low-viscosity liquids to pastes to solid, depending upon the precise combination of molecular weight and EO:PO ratio (higher molecular weight and higher EO proportion increasing the melting point). See review by Schmolka (J. Am. Oil Chem. Soc., 54:110-116, 1977).

In BASF's PLURONIC® code, the alphabetical designation is derived from the physical form of the product at room temperature: L for liquids, P for pastes, and F for flake (solid) forms. In the numerical designation, the first digit (or the first two digits in a three numeral code) multiplied by 300 indicates the approximate molecular weight of the hydrophobe. The last digit multiplied by 10 indicates the approximate percentage (w/w) of the hydrophile in the PLURONIC® copolymer. Preferred block AOC are poloxamer 108 (PLURONIC® F38), poloxamer 188 (PLURONIC® F68), poloxamer 238 (PLURONIC® F88), poloxamer 288 (PLURONIC® F98), poloxamer 338 (PLURONIC® F108), poloxamer 237 (PLURONIC® F87), poloxamer 335 (PLURONIC® P105), and poloxamer 407 (PLURONIC® F127).

Poloxamer 188 (PLURONIC® F68) (8350 g/mol, 80% POE), has been used for topical wound cleaning and has been approved for intravenous use as an emulsifier for perfluorocarbon oxygen-carrying formulations. Aqueous solutions of a poloxamer such as poloxamer 407 (PLURONIC® F127) (12,500 g/mol, 70% POE) at a sufficiently high concentration (typically greater than about 30% w/v) are used as hydrogel formulations for drug delivery. These are preferred block AOC.

Poloxamines (e.g., TETRONIC® block copolymers from BASF), are 4-armed symmetrical poly(alkylene oxide) block polymers prepared using an ethylene diamine initiator with the general formula $[(EO)_x\text{-}(PO)_y]_2\text{-}NCH_2CH_2N\text{-}[(PO)_y\text{-}(EO)_x]_2$, and are another example of an alkylene oxide copolymer that may be used to make the composition. Reverse poloxamines, in which the four PEO blocks are added before the four PPO blocks, can also be used.

Blending Random and Non-Random Alkylene Oxide Polymers

A discovery that forms one basis for the present invention is that certain random AOC are capable of forming either compatible or miscible blends (i.e., alloys) with selected solid AOH and block AOC. This previously unrecognized property differentiates random AOC from other liquid polymers, such as low molecular weight PEO and PPO, which do not form alloys with solid PEO or poloxamers, or liquid poloxamers, which will generally only form alloys with closely related copolymers, such that no advantage is to be gained by the mixing. Adjustment of the mass ratio between non-random polymer and random copolymer can be used to produce compositions of varying hardness and viscosity. For compositions, the mass ratio (block AOC: random AOC) may be 1:199 to 199:1. A mass ratio of about 2:98 with 22K random AOC is no longer a flowable liquid, while a mass ratio of about 1:19 with 22K random AOC is a solid. The mass ratio may be at least about 1:4, about 1:3, or about 1:2; the mass ratio may also be not more than about 2:1, about 3:1, or about 4:1. The compositions may be further described by intermediate ranges using the aforementioned upper and lower limits.

The mechanical properties of most polymers need to be adjusted by the inclusion of plasticizers to make them suited to their intended use. Plasticizers are used to make the polymer softer, more malleable or ductile, and less brittle, and must be miscible with the polymer to fulfill this function. Most plasticizers are small molecules, which by their nature, are often toxic or non-biocompatible and easily released from the polymer. A polymeric plasticizer would be very valuable for many applications, especially one that was biocompatible, not toxic, not metabolized, and rapidly eliminated. Polymeric plasticizers for solid alkylene oxide polymers and copolymers have not previously been described. Our extensive efforts to find a suitable biocompatible material that could be used as a softener or plasticizer eventually led to the identification of a specific molecular weight range of random AOC which forms compatible or miscible blends (i.e., polymer alloys) with block AOC and AOH (see Tables). The finding that a liquid random AOC could be used in combination with a solid non-random PAO to form a novel polymer alloy with commercial utility was unanticipated and has not, to our knowledge, previously been described.

Polymer alloys can be made with handling characteristics that range from a grease-like consistency to a hard wax. The different levels of malleability and plasticity can be achieved largely by altering the choice of components and their proportions as outlined in the Examples and Tables. The various other embodiments are made in a similar manner. The solid AOH or block AOC copolymer component is normally not dissolved by the liquid random AOC component at room temperature. A polymer alloy can be made, however, as follows: The solid component is brought to its molten state by the application of heat. The random AOC component is heated to the same temperature, and the two components are thoroughly mixed by stirring in the molten state. Upon cooling, the AOC alloy is formed. Altering the cooling rate can also be used to adjust the handling characteristics and structure of the AOC alloy.

A non-flowable composition can be made with a relatively small amount of the solid block AOC component. As an example, an alloy containing 2 parts by weight of the solid poloxamer 188 to 98 parts of the liquid 22K random AOC does not flow at room temperature (see Tables). On the other hand, a hydrogel made from poloxamer 188 and water would require 30% of the solid to form a non-flowable gel at 37° C., but would still flow at lower temperatures.

The compositions may alternatively be formulated in solid or liquid form (e.g., milling, agitating, kneading, or stirring), but heating of the composition is preferred to achieve uniformity with solid or viscous forms. The composition may be sterilized by standard techniques such as autoclaving or irradiation. It may be molded by hand; applied with a brush, flat or shaped rod, or syringe; formed into a bar or stick; or implanted/placed in the body. A device may be coated or a bioactive agent mixed with excipient. Malleability, thermoplasticity, and viscosity may be measured by methods known in the art. Similarly, bio-compatibility and non-toxicity may be assayed by methods known in the art.

In one preferred embodiment, the composition is made by mixing a 1:1 ratio by weight mixture of a block AOC that is a solid at room temperature, such as poloxamer 188, with a random AOC, such as 22K random AOC, that is a liquid at room temperature. However, a range of physical properties for the AOC alloy can be created depending on their intended use (see Tables).

In its anhydrous state, poloxamer 407 (PLURONIC® F127) is a hard solid, and it is available as a gritty powder or in flake form and as such is not very useful. Adding even small amounts of the 22K random AOC softens the hard material, producing a homogeneous wax or soap-like material with improved handling characteristics, but with the surfactant and other properties similar to those of the original poloxamer 407. With increasing concentrations of the random AOC, the composition becomes more malleable.

Conversely, 22K random AOC is a flowable, viscous liquid at room temperature. By addition of as little as 2% (w/w) of poloxamer 188, a polymer alloy is formed which handles like a greasy solid and does not flow at room temperature.

It is anticipated that other synthetic AOC will be developed and become commercially available. It may be feasible, for example, to make compounds containing AO chains that do not fall clearly into the scope of the claims. It is conceivable that a high molecular weight compound that is a liquid at room temperature could be made that would fall outside the strict classification of a random AOC, or that a AOC essentially solid compound may not be strictly composed of blocks. It is entirely conceivable that a PAO copolymer could be made to contain sections of a block copolymer and a random copolymer. Such equivalents should be included within the scope of protection.

Medical Utilities

Some embodiments relate to an adhesive material that can be used in orthopedic surgery, dentistry, reconstruction, spinal and craniofacial surgery, and other surgical applications because of its improved properties. Numerous uses include bone hemostasis agent or as an adhesive agent that can, for example, facilitate the adherence of a screw to the blade of a screwdriver. In one preferred embodiment, a polymer alloy is made using a 1:1 ratio of NF grade poloxamer 407 (PLURONIC® F127NF) and 22K random AOC. The handling characteristics of this formulation make it especially useful as a bone hemostasis agent, as the sticky, cohesive wax adheres well to bone, even when the surface of the bone is wet. In contrast to the prior art, preferred embodiments provide a biocompatible, substantially non-toxic, stable (i.e., non-metabolizable and readily eliminated) polymer alloy with superior handling characteristics.

Porous implant materials are useful for the repair or reconstruction of the bony skeleton. Implants can be used to fill bony defects, or they can be to augment or replace bone or cartilage in humans or in animals. Porous implants with a pore size of 60 microns or greater exhibit tissue ingrowth into their pores. Collagen is deposited within the pores and forms a highly static complex, which is resistant to infection and exposure. For a porous composition to be effective as an implant material, it must fulfill four criteria: (1) biocompatibility, (2) the pores must be large enough to allow for tissue ingrowth, (3) the pores must interconnect, and (4) the structure of the implant must be both permanent and rigid enough to maintain the porous framework under conditions encountered at the implanted site, To be useful, the material must also be sufficiently easy to use in a clinical setting. It is also desirable for the material to be non-toxic, have a relatively long shelf life, be relatively economic, and have good handling characteristics. There is a need to improvement the handling characteristic and to add a resorbable composition to fill or cover the pores. Filling or covering the pores would allow the implant to glide through tissue planes and would keep debris from entering the implant.

Therefore, a further object is to create a porous implant whose pores are filled or covered with a resorbable substance.

Porous implants used in humans and animals are made by sintering solid particles such as polyethylene, PMMA, or titanium; or they are adapted from naturally substances such as coral in the case of porous coralline hydroxyapatite. Polyethylene, a biologically inert material, has numerous applications in surgery. It is a straight-chain hydrocarbon synthesized by the polymerization of ethylene. Hydroxyapatite and tricalcium phosphate are similar in composition to the major mineral component of bone and may be resorbed or remodeled, depending on their formulation. Methacrylate- and silicone-containing particles are not preferred for use.

Placement of porous implants into one or more bone defects is a common surgical procedure. Implant materials that allow for bone to grow into the pores are considered to be osteoconductive. Implants that have a bioactive component that induce bone formation, such as implants made from a bone removed from a different location, are considered to be osteoinductive. In the event that it is desirable that native bone eventually replaces the implant, material that can be remodeled by the body may be preferable. In certain clinical situations, such as a defect in the adult human cranium, the bone is not expected to grow, and a non-resorbable formulation is preferable. Studies have shown that in the craniofacial skeleton, a number of commonly used solid implants cause bone resorption adjacent to the site of implantation. Porous implants may not have the same effect.

The majority of porous implants that allow for tissue in growth are grossly solid structures with a microporous structure. To be clinically useful, they often need to be sculpted by the surgeon into their desired form. The microporous structure of the implant can cause the implant to adhere to tissue, much like a piece of VELCRO hook-and-loop fastener, making the implant placement difficult. Debris deposition into the pores is another undesirable drawback to the use of porous implants. To decrease the risk of bacterial infection, the implant may be soaked in an antibiotic solution prior to use.

An implant whose pores are filled with a biocompatible excipient would be an improvement over the implants in current clinical use. Temporarily filling those pores until such time as in growth of tissue occurs would eliminate the accumulation of debris within the implant and could decrease the incidence of bacterial infection. Temporarily filling the pores using an appropriate excipient would also improve its handling characteristics to make the implant more lubricious and less damaging to tissue, thus allowing the implant to slide along tissue planes during surgical placement. The appropriate excipient could then also become adherent in the presence of body fluids and lessen the incidence of malpositioning that can occur after implant placement. The biocompatible excipient could also serve as a carrier for therapeutic products. For example, chemical compounds could be released over time as the excipient is resorbed.

A preferred carrier or excipient should be biocompatible, non-toxic, non-metabolizable, readily eliminated, relatively economic, and have good handling characteristics. The composition may allow an implant to be lubricious to glide along tissue planes, but it should also enable the implant to become adherent to surrounding structures when its final position is attained. Cohesion may be used to temporarily hold tissue together until more permanent attachments may be made. An anhydrous formulation might increase the half-life of a biological agent and reduce the risk of contamination.

In a preferred embodiment, water-soluble bone wax is applied to the surface of a porous implant, for example a coralline, porous hydroxyapatite implant, which would cause the implant to become slippery when in contact with tissue fluids, thus facilitating the placement of the implant by reducing the adherence of the surrounding soft tissue.

In another preferred embodiment, a porous implant can be made so that its pores are largely or completely filled with a resorbable polymer. This could be achieved, for example, by placing a porous polyethylene implant into a molten polymer composition under a vacuum, and then allowing it to cool. The resulting implant would glide along tissue planes, it would remain flexible, and it would be resistant to having debris collect within its pores. Once implanted, vascular and soft tissue ingrowth into the pores of the implant could occur as the polymer alloy is resorbed.

The prior art teaches the use of random AOC as lubricants with a high affinity for metal surfaces. But random AOC are liquids which, like oils, will flow away from surfaces unless continuously replaced. To formulate a grease which will remain in place for lubricating bearings and the like, manufacturers of such products will often combine an AOC or AO homopolymer base stock with an ionic soap, usually lithium, calcium, or sodium based. There is an unmet need for a non-flowable, non-ionic, non-corrosive, and completely water-soluble grease-like lubricant, particularly one that is biocompatible and suitable for use in medicine and surgery. In another embodiment, a water-soluble composition is used as a non-flowable, non-corrosive, and water-soluble lubricant.

During surgery, lubrication of instruments or other devices is usually limited to physiological saline and the patient's own fluids. Use of lubricious substances derived from human or animal sources risks an immune response and the transmission of infectious agents. There is a need for a safe, biocompatible, inexpensive carrier that could be used as a surgical lubricant that can be applied when needed. Such a lubricant could decrease tissue injury and/or improve the handling characteristics of devices as they are passed through tissue. Examples of injuries caused by surgical instruments are abrasive tissue burns caused by endoscopic instruments as they are moved along narrow tissue planes. Surgical implants, such as those made from porous polyethylene, are especially difficult to pass along tissue planes, since soft tissue tends to adhere to these implants. Breast implants, especially those with a textured surface that are placed through small, remote incisions, can be very difficult to place without sufficient lubrication, Thus, the composition may be used as a carrier for devices (e.g., implants, instruments) to ease insertion.

In one embodiment, the AOC alloy can be used as a lubricant and/or protectant. For example, a polymer alloy made using a 1:19 ratio of NF grade poloxamer 407 (PLURONIC® F127NF) and 22K random AOC could be applied to the surface of a steel surgical instrument, prior to the instrument being used in surgery. The polymer alloy would serve as a protectant, and would have the advantage over prior art in that it is not liquid, therefore it would not flow, nor would it be absorbed by cloth that typically comes in contact with surgical instruments. It would have the added advantage of being completely water-soluble and non-toxic. Once used in surgery, in the presence of tissue fluids, the surface of the instrument would become lubricious, which would enhance the ability of the instrument to glide along tissue surfaces.

Another embodiment is an adhesive material comprised of a matrix (e.g., PEO, or a block AOC copolymer or a random AOC copolymer, or a combination thereof) combined with a porous or solid filler for use in surgery.

In a number of clinical applications, it is advantageous to construct a porous structure by placing an aggregate of solid particles or granules that become fixed in into their desired location by the in growth of soft tissue into the spaces between the particles. Allograft bone is a substitute source for solid particles. It is readily available and precludes the surgical complications and patient morbidity associated with autologous bone as noted above. Allograft bone may be considered a collagen fiber reinforced hydroxyapatite matrix containing active bone morphogenic proteins (BMP) and can be provided in a sterile form. The mineral component may be removed from bone to form a demineralized bone matrix (DBM). Such DBM is naturally both osteoinductive and osteoconductive. Once surgically implanted, DBM is fully incorporated in the patient's tissue and it has been used in bone surgery to fill osseous defects. DBM is usually available in a lyophilized or freeze-dried and sterile form to provide for extended shelf life. The DBM in this form is usually very coarse and dry, and is difficult to manipulate by the surgeon. It is known that DBM can be supplied in a matrix of low molecular weight solvents, but these are know to be toxic to the surrounding tissue, and they form a runny composition.

Therefore, one embodiment is to use the composition as a matrix for DBM. As an example, a composition containing a 1:2 mass ratio of poloxamer 407 (PLURONIC® F127NF) and 22K random AOC can be used. The resultant DBM putty has superior handling characteristics and will adhere DBM to the intended site, it is non-toxic to surrounding tissue, and it contains no water that could inactivate the bone morphogenic proteins in the DBM.

Inorganic materials can also provide a matrix for new bone to grow at the surgical site. These inorganic materials include hydroxyapatite obtained from sea coral or derived synthetically. Either form may be mixed with the patient's blood and/or bone marrow. Hydroxyapatite granules may be used as bone inlays or onlays. The granules can be mixed with microfibrillar collagen and blood from the patient. Although the mixture is termed a "paste" herein, it may also be described as a gel, putty, or slurry depending on its handling characteristics.

Particles with sizes (i.e., the largest dimension) in the range from about 35 microns to about 500 microns (or about 50 microns to about 150 microns) are desirable to minimize the possibility of particle migration by phagocytosis and to facilitate injectability. Phagocytosis occurs where smaller particles on the order of 15 microns or less become engulfed by the cells and removed by the lymphatic system from the site where the augmentation material has been introduced into the tissues, generally by injection. At the lower end, particles greater than 15 microns (typically 35 microns or above) are too large to be phagocytosed, and can be easily separated by known sizing techniques (e.g., filtration, gel exclusion, molecular sieving). For a population of substantially spherical particles, the diameter may range from about 35 microns to about 500 microns for at least the majority of the population. Thus, it is relatively simple to produce narrow or equivalent particle size ranges that are desirable for use.

Particles may comprise at least about 10% (v/v), at least about 25% (v/v), not more than about 40% (v/v), not more than about 64% (v/v), or combinations thereof. The composition may be kneaded or otherwise worked to obtain a homogeneous distribution of particles within the composition. Such working is avoided, however, if a non-homogeneous distribution is desired and different compositions may even be laminated together.

As an example, polyethylene particles ranging in size from 50 to 300 microns are blended with a composition containing a 1:2 ratio of poloxamer 407 (PLURONIC® F127NF) and 22K random AOC. The resultant polymer putty can be used to fill cranial defects. The matrix performs two important tasks: it forms a cohesive putty and serves to adhere the particles to the intended site of implantation. In this regard, the composition is superior to the prior art.

Excipients are biologically inactive substances that are associated with, often in combination, drugs, devices, and other therapeutic agents to make a therapeutic product. They may be classified by the function(s) they perform as binders, disintegrants, fillers, diluents, suspending agents, dispersing agents, lubricants, flow enhancers, softeners, plasticizers, and coatings. Although biologically inert, they may be critical and essential components of a therapeutic product. They might be used to reduce lability of a bioactive agent, enhance bioavailability, and/or control the location and rate of release of the bioactive agent. They also may be required to deliver a pharmaceutical formulation by a desired route, whether oral, parenteral, enteral, or topical and, if appropriate, to enhance the appearance and palatability of the product. In many therapeutic products, excipients make up the bulk of the total dosage form. The excipient can be sterilized prior to formulation by autoclaving or irradiation, or the formulation may be sterilized as part of its production. In addition, a vehicle may be included in the therapeutic product. It may be water, another aqueous solution with buffer and/or physiological salts, non-aqueous solution, emulsion, or suspension. The device may be a filler, anchor, catheter, implant, plate, prosthesis, screw, suture, surgical instrument, or the like; it may be made from bone (e.g., chips or powder) or a derivative thereof (e.g., demineralized bone), ceramic (e.g., calcium salt especially hydroxyapatite), glass, polyethylene, or metal (e.g., stainless steel, titanium). The drug may be a bone growth factor or morphogenic protein, hormone, other protein, nucleic acid (e.g., DNA, RNA, analogs or mixtures thereof), analgesic or anesthetic, antibiotic, antiseptic, narcotic, steroidal or nonsteroidal anti-inflammatory agent, or the like.

The compositions are also well suited as carriers or excipients for delivery of bioactive agents, medical/surgical devices (e.g., implants and instruments), and other therapeutic (e.g., non-polymeric) products. Articles may be coated with carrier or chemicals may be mixed with excipient. Sterilization may be performed in an autoclave or by irradiation for use in vivo.

Bone morphogenic proteins (BMP) and TGF-beta are two examples of bioactive substances. Other differentiation factors, stem cell factors, antibiotics, antibodies, antigens, chemotherapeutics, cytokines/chemokines, enzymes and their substrates (e.g., activators, inhibitors, or reactants), receptors (especially secreted forms and mimetics thereof) or their ligands (e.g., agonists or antagonists), signaling molecules (e.g., mediators of a signal transduction pathway, agonists or antagonists thereof) may be formulated in a composition with the composition.

For use as a carrier or excipient, the attributes of being biocompatible, substantially non-toxic, simple to manufacture, and readily eliminated by a human or animal are important. In addition, the composition may solubilize hydrophobic compounds and thereby release them into solution. An anhydrous formulation has the benefit of providing a stable excipient to those bioactive agents that are labile in an aqueous environment. Furthermore, if water is present, the composition serves to bind the water to make it unavailable to interact with the bioactive agent. Water-insoluble compounds may be incorporated into a polymer composition, and then administered to a subject. There is no prior art known to have these attributes.

Examples of a carrier or excipient are (1) polymer alloy containing a 1:2 mass ratio of poloxamer 407 (PLURONIC® F127NF) to 22K random AOC and (2) polymer alloy containing a 1:1 mass ratio of poloxamer 188 (PLURONIC® F68NF) and 22K random AOC.

Certain vectors, such as viruses and infectious particles, likewise are in need of an excipient that is free of water. One embodiment is to provide an excipient for biological vectors that is biocompatible, substantially non-toxic, and may be formulated to contain no water. Such an excipient has utility in delivering vectors to cells, tissue, organs, animals, and plants.

Joints of some surgical instruments (e.g., scissors and clamps) typically need to be cleaned and the joints need lubrication. Such instruments can be dipped in instrument milk prior to their use in surgery. Thus, in addition to use as a detergent, the composition may be used as a lubricant. The effectiveness of a composition as instrument milk may be enhanced because of its biocompatibility, flowability, substantial non-toxicity, and water solubility.

As described above, a composition may be used as excipient for drug delivery or in the manufacture of other bioactive agent-containing compositions to deliver such compounds to a subject though a variety of routes, including percutaneous, enteric, intranasal or respiratory, topical, and through mucous membranes (e.g., rectum). When ingested orally in sufficient quantity, the composition may have biological activity of its own due to the ability to draw water into the gastrointestinal tract and act as a laxative.

Open wounds, particularly those that are infected or have a tendency to seep fluid, continue to be a difficult management problem for health care providers. The aims of wound care management in these situations include keeping the wound moist, thus optimizing the conditions for the wound to heal; removing excess fluid and debris from the wound; and minimizing or treating infections. It would be advantageous for a component of the wound dressing to remain moist, have the ability to remove or absorb excess fluid, and be formulated to include an antimicrobial agent. Thus, one embodiment provides such a substance for wound care.

There are a variety of topical formulations encompassing creams, gels, and ointments, including sun blocks and wound dressings. There is an unmet need for a lubricious component which absorbs water and is thus beneficial in treating seeping wounds and stasis ulcers. The composition may be packaged in a bottle or tube, applied to the wound, and then optionally covered by a occlusive or non-occlusive dressing. Alternatively, it may be prepackaged with the dressing under aseptic conditions.

Therefore, in some embodiments, the composition may be used as a laxative or wound dressing.

Nonmedical Utilities

Wax is an organic, plastic-like substance that is solid at 25° C. and melts to a liquid when heated. Because wax is plastic in nature, it deforms under pressure without the application of heat. The term "wax" is applied to a large number of chemically different compounds, and it has come to include compounds that are soluble in water. These waxes are said to have the properties of aqueous dispersion. U.S. Pat. No. 6,554,052 teaches the use of a water-soluble wax to decease the amount of precious metal in the production of jewelry and its utility in the 'lost-wax' casting process. There is a need for improvement in the handling characteristics and the ease of manufacture of water-soluble waxes.

In one embodiment, the composition is used as a wax.

There is a need to formulate crayons and pastels to be non-toxic and washable with water. U.S. Pat. No. 4,978,390 teaches a composition in the form of a crayon or marking pencil lead which is washable from fabrics, wallpaper and painted surfaces. A preferred embodiment of the composition contains an epoxide derivative of a poly(ethylene glycol) resin. Such a composition has the disadvantage of leaving residue after the application of water. There is a need for a simple, inexpensive, substantially non-toxic, water-soluble crayon.

Appropriate compositions (e.g., a polymer alloy of about three parts by weight of poloxamer 338 and one part by weight of 22K random AOC) produce a medium-hard wax that is not brittle and which can be rubbed onto a surface such as paper, without flaking or fracturing, like a regular wax crayon. A wide range of harmless dyes can be used to color the composition, including those presently used to color the regular types of children's wax crayons, simply by mixing with the molten polymer mixture prior to casting the material into an appropriately-shaped crayon mold. The crayon thus formed is made from only two inexpensive components plus dye, is non-toxic, and has the utility of a regular crayon for drawing but is fully water soluble. When added as a fine powder to the molten composition, many hydrophilic dyes (e.g., methylene blue) are dispersed but not dissolved. Crayons formulated in this way can have a pale, slightly mottled appearance. In use, these crayons only faintly mark the paper. However, since the crayon wax is water soluble, subsequent application of a small quantity of water to the paper results in the development of bright, saturated colors often quite different from the apparent color of the crayon used. Thus, these compositions have utility as novel art materials. A further obvious benefit of the water-soluble crayon is the simplicity of clean-up if the crayon is misused. Washable dyes and other colorants are used as pigment.

In another embodiment, the composition is used to as a carrier for a color pigment that could be used in the manufacture of washable crayons.

Poloxamers and other detergents have been used to sterilize surfaces and materials, Such agents are usually in powder or flake form. There is a need for a non-ionic soap, detergent, or stain remover which has the utility of poloxamers, including the ability to perform in solutions with a high mineral content (e.g., hard water) or solutions of high salinity (e.g., such as brackish water or seawater), and can be provided in an advantageous physical form with improved handling characteristics, such as a solid bar or rub-on stick. Here, the composition provides the surface active functionality of a non-ionic detergent in a convenient, easy to use form.

The surfactant properties of the composition are of benefit when a non-ionic cleanser or stain remover is needed. Such a cleanser is of benefit in that it is environmentally safe, does not leave soap scum, and will perform in hard water and saltwater environments. As an example, an alloy of about of 60% by weight of poloxamer 188 and 40% by weight of 22K random AOC can be melted and cast into a bar form, preferably similar to the shape of a standard bar of soap. The formulation can be used as a cleanser bar, and has an appearance very similar to glycerin soap, which can be further enhanced by including other cleansing agents, boosters, colorants, fragrances, and moisturizers in the formulation if so desired. The main value of this embodiment is that the non-ionic surfactant property of poloxamer 188, which in its regular form is a hard white granular material, can be applied to tasks for which it has not been previously used, such as hand washing, in a familiar, simple and convenient bar form. Other poloxamers or similar block copolymers can also be used in place of the poloxamer 188. The non-ionic soap bar is effective for use as a mechanic's hand cleaner for removing oily and greasy grime, will work with hard water without producing soap scum, and can be used in saltwater.

Aqueous release agents are used in applications such as molding. There is a need for a non-toxic, non-corrosive, water-soluble, non-flowable, and inexpensive release agent that will adhere to a surface but will release on demand, such as when placed into an aqueous environment.

In one embodiment, a water-soluble composition is used as an aqueous release agent.

For use as a water-soluble, non-petroleum-based, synthetic lubricant, the composition can be formulated in any number of different grades from a hard wax to a soft grease simply by varying the proportions of the components. A blend of about 30% (w/w) of a random AOC, such as 22K random AOC, and about 70% block AOC, such as poloxamer 188, cast into a simple stick form (e.g., in a retractable tube) provides a medium-hard lubricant stick that can be rubbed on where needed or applied safely directly to moving surfaces, cutting tools (e.g., saw blades, drill bits, planing machines) or parts of machinery. The water-soluble, non-oily nature of the composition is useful to prevent damage or staining when machining delicate materials or wood, and simplifies clean up. The composition has further advantages when used as a metal lubricant because the random AOC component is attracted to, and plates out on, hot metal surfaces. The non-corrosive properties are also a benefit for metal working applications.

A medium blend of about 40% of 22K random AOC, about 60% of poloxamer 188 can be used in bar or stick form as a rub-on lubricant for the underside of skis, snowboards and the like. For this application, the lack of toxicity, proven environmental safety, and non-corrosive nature of the component materials are especially advantageous.

As an example of a grease, 95% to 98% of 22K random AOC and 2% to 5% of poloxamer 188 were blended to provide a stiff to soft semi-solid grease, which does not flow under gravity at room temperature. It is a useful grease alternative, especially for lubricating metal parts, because it is less labile than natural or petroleum-based oils, with the additional benefits of being water soluble, biocompatible, and substantially non-toxic. With very low amounts of block AOC, the blend may become a viscous, somewhat sticky, oily liquid which has utility as a lubricant.

Any lubricant composition can also be used as a carrier for other friction modifiers (TEFLON particles, colloids, etc.), including potentially useful friction modifiers that are not readily oil soluble.

EXAMPLES

The following examples more particularly describe the invention but are intended for illustrative purposes only, since modifications and variations will be apparent to those skilled in the art.

Example 1

Characterization of Polymer Compositions

Specific characterization of various embodiments can be ascertained by using various specialized techniques (e.g., high-sensitivity differential scanning calorimetry), which can be used to probe the precise nature of the alloy and the interaction between the component molecules. In particular, the miscibility may be confirmed by alterations in the glass transition temperature (Tg) of the alloy relative to the Tg of the individual components, if the Tgs of the individual components are sufficiently different. However, such measurements on polymer mixtures can be very difficult to make and interpret, even by experts in the field. If good results are obtained they are often strictly limited to the precise composition, volume fraction and temperature at which the measurement was made and, even with the best theoretical analysis, these data may have little predictive value for other combinations of polymers, even with only slight differences in the molecular weight or structure. Thus, it proved more expedient to screen the polymer blends by direct observation both macroscopically and microscopically, to determine which combinations provides the desired combination physical properties, and to determine whether the polymers are compatible or miscible on the microscopic scale, as follows.

Non-random AOH or AOC and random AOC were blended together in various proportions. Appropriate amounts (w/w) of each polymer were placed in a glass container to prepare 10 g of polymer mixture, and heated in a microwave for 60 to 90 seconds to melt the solid component (the time was varied as necessary for the polymer mixture to reach approx 80° C.). After thorough mixing, the samples were centrifuged at 500 g for 2 minutes to eliminate any air bubbles. All samples had a water-clear appearance in the molten state at 80° C.

For macroscopic evaluation, the molten polymer blends were reheated to 80° C. and cast into small bars by pouring into individual aluminum molds of 2 inch×0.75 inch×0.1 inch deep, and held at 4° C. until fully set (less than 5 min). The appearance and mechanical properties of each sample were evaluated visually and by hand molding in a manner simulating some of the intended applications of the polymer alloy. For the microscopic testing, 15 µl to 20 µl of the melt was pipetted onto a glass microscope slide on a thermostatically controlled hotplate. A coverslip was placed on top of the melt and slight pressure applied to cause the polymer blend to flow just to the edges of the 25 mm×25 mm coverslip, to form a consistent thin layer. The slide was then removed from the hotplate and examined under the microscope. Copolymer spherulites or immiscible blends were photographed at 10× magnification. A differential interference contrast system (crossed polarizers) was used to enhance the characteristic birefringence pattern (Maltese cross) displayed by spherulite crystals.

Three random copolymers were evaluated: a three-branched 22K g/mol random AOC (22K random AOC) with an EO:PO ratio of 1:1 (BASF Pluracol® V-10); a linear 12K g/mol random AOC (12K random AOC) with an EO:PO ratio of 3:1 (Sigma-Aldrich #43,820-0), and a linear 3.9K g/mol random AOC (3.9K random AOC) with an EO:PO ratio of 1:1 (Dow UCON 50-HB-5100). The non-random copolymers were selected from a range of Pluronic® block copolymers (F68, F88, F98, F108, F87, F127) and PEO (homopolymer) fractions of various molecular weights (about 1.5K, 2K, 3.5K, 5K, 7.5K, 12K, 20K, and 35K g/mol).

The macroscopic properties of the polymer combinations are described in the Tables, including both descriptive data and a semi-quantitative ranking for each property of interest, for which the 1:1 alloy of F68 and V-10 was used as a reference point. The data show the ranges of compatibility for different types and molecular masses of poloxamers and PEO molecules with each of the three random copolymers.

For the 22K random copolymer, macroscopically compatible blends could be made with F68 (poloxamer 188) over a wide range of proportions, from 2% to 98%, with no evidence of incompatibility. The blends with a low proportion of F68 (2% and 5% in Tables) resembled clear, colorless greases, while the others were waxy solids, ranging from very soft to very hard, similar in appearance to other forms of wax (e.g., paraffin wax or candle wax). The handling properties of the alloys tracked the polymer proportions closely, with hardness increasing and malleability and ductility decreasing with increasing F68 content over the range from 2% to 80%. Mixtures of 22K random AOC with F88, F98, F108, F87 and F127 were also evaluated in selected proportions. Relative to the F68 compositions, each of the other block copolymers conferred slightly different and potentially useful characteristics to the composition For example, a 50:50 mass ratio of F127 block copolymer to 22K random AOC produces an alloy that was softer, more malleable, and tackier than a similar composition of F68 block copolymer and 22K random AOC, and had an attractive white opaque appearance while the F68 composition was clear. Other differences are apparent from the data in the Tables.

The compatibility of PEO in combination with 22K random AOC was a function of the PEO molecular mass. Thus, macroscopically compatible blends were obtained for PEO of 1.5K g/mol to 5K g/mol, but 7.5K g/mol was minimally or not compatible and 12K g/mol PEO was clearly incompatible with the 22K random AOC, as indicated by a grainy texture and lack of cohesion of the blend. The compatible PEO compositions were generally similar to the block copolymer compositions, but tended to be softer and more ductile, and to have a different "feel", i.e., more oily to the touch and a gum-like tackiness.

The 12K random AOC random copolymer also formed alloys with the same block copolymers and PEO homopolymers (2K, 3.5K, and 5K) and was incompatible with PEO samples of 12K and above. The 12K random AOC alloys were almost identical in terms of mechanical properties and appearance with the equivalent 22K random AOC compositions. In contrast, the lower molecular weight random EO:PO copolymer, 3.9K random AOC, was not compatible with any of the block copolymers or homopolymers evaluated in the study: although apparently completely miscible at 80° C., the blended polymers separated on cooling, forming a two-phase system of hard crystalline grains of the non-random polymer in a sticky or liquid carrier (predominantly the 3.9K random AOC). These results indicate that higher molecular weight random AOC are necessary to form compatible blends with block AOC and PEO: the threshold presumably lies between about 4K g/mol and about 12K g/mol.

Although most of the AOC polymer combinations formed macroscopically homogeneous materials, the microscopic studies were necessary to provide confirmation of the compatibility of the polymer phases. FIG. 1 shows low power (125×) views of alloys of 22K random AOC and F68, in proportions from 2% (w/w) to 98% (w/w) after cooling. Looking first at the 20% (w/w) to 60% (w/w) samples, each image is very similar, with each spherulite crystal extending through the material to meet adjacent spherulites along very precise boundaries without any gaps or spaces. From 2% (w/w) to 10% (w/w) F68 blends, the spherulites are less distinct due to the lower amount of the crystal-line F68, but it is apparent that the size of the spherulites is the same and again, there are no gaps or other defects. Above 60% (w/w) F68, there is an increase in the spherulite size, and lines (dark under the microscope) appear between the region between the spherulites. Observation of the polymer blend while cooling revealed that these lines are in fact negative defects that appear suddenly in the liquid phase between the advancing spherulite boundaries, presumably due to the sudden nucleation of a gas bubble under the negative pressure resulting from the contraction of the material. These bubble defects appear to be the cause of the increased whiteness and opacity of the alloys with increasing F68 content, The regularity of the spherulite structures and the absence of 22K random AOC-filled spaces between the spherulites indicates that the material is effectively a single phase, with the two polymers completely and intimately associated with each other at least on the micrometer level.

FIG. 2 shows a 1:1 mass ratio of random copolymer and non-random polymer. FIGS. 2A-2B are from compatible alloys—note the even spherulite pattern, and the absence of any defects. FIGS. 2C-2E are examples of incompatible and immiscible compositions. Several distinct phases are seen—some large spherulite crystal domains of the PEO interspersed with large clear globular regions of the random copolymer, within which are additional smaller droplets of PEO which have crystallized into shapes corresponding to the interface of the phase-separated droplet.

Thus, we have defined the range of compatibility for combinations of random and non-random alkylene oxide polymers, making possible the creation of polymer compositions with a range of very useful material properties. The results further indicate how to select the precise types, molecular masses, and proportions of the component polymers to tailor the material properties of the composition to satisfy the desired specifications. The discovery of compatible combinations of these types of polymers, and identification of appropriate molecular weight ranges for the component polymers is novel and unexpected, and is not taught by any of the prior art.

Example 2

Polymer Composition for Bone Hemostasis

A preferred composition with utility as a bone hemostasis agent may be produced in the following manner: Equal quantities by weight of NF grade poloxamer 188 (PLURONIC® F68NF) and 22K random AOC are sealed in a heat-resistant glass container and heated to a temperature of 80° C. in an oven. The contents of the flask is stirred for a period of 8 hours at 80° C. The liquid composition is allowed to remain undisturbed for another 16 hours at 80° C. to allow air bubbles to escape from within the liquid. The liquid is then dispensed directly into TEFLON coated metal molds maintained at a temperature of 80° C. The molds are cooled to 4° C. for 15 minutes. The solid polymer composition is removed and placed into individual foil packets lined with a polyethylene coating. These packets are then placed into pouched appropriate for packaging sterile implantable devices. The product is sterilized using an appropriate dose of plasma radiation.

A study was performed comparing the long-term effects of AOC wax and commercially available beeswax in paired cranial defects in the adult rat. Two defects 4 mm in diameter were hand cut using a dental drill through the parietal bones on either side of the midline in 10 Sprague-Dawley rats. The materials used were in the shape of disks 4 mm in diameter and 1.0 mm thick, and were either AOC wax comprised of equal quantities by weight of NF-grade poloxamer 188 (PLURONIC® F68NF) and 22K random AOC, or beeswax (Bonewax, Ethicon, Inc.). Both materials were implanted into each rat. At surgery, the two materials exhibited no difference in their handling characteristics and hemostatic effects. Animals were sacrificed at 7 days, 30 days, 60 days, and 90 days. On gross inspection, the beeswax remained present in each animal and there was no remaining AOC wax. There were no visible ill effects of the AOC wax. After formalin fixation, plain radiographs (16 inch distance, 50 kV for 0.1 sec) were obtained. No ill effects of the AOC wax on bone healing could be seen upon examination of the radiographic images. The bones specimens were then decalcified in 5% acetic acid for 7 days, embedded in paraffin wax and sectioned for hematoxylin and eosin (H & E) staining. Upon microscopic examination of the specimens, there was no evidence of deleterious effects of the AOC wax on bone healing, the local tissue or the underlying brain.

Example 3

Non-Toxicity of Polymer Composition

The biocompatibility of the composition was demonstrated by assessing intracutaneous reactivity, systemic toxicity, cytotoxicity, hemolysis, mutagenicity, and the potential for chromosomal aberration. The composition used for all tests was composed of equal quantities by weight of NF-grade poloxamer 188 (PLURONIC® F68NF) and 22K random AOC.

The composition was evaluated for intracutaneous reactivity to test for potential irritation and sensitization. A 0.2 ml dose of the material was injected by the intracutaneous route into five separate sites on the backs of rabbits, along with controls. Observations for erythema and edema were conducted at 24, 48, and 72 hours after injection showed no evidence of irritation. The primary irritation index characterization for the composition was negligible.

The composition was evaluated for systemic toxicity in accordance with the guidelines of the United States Pharmacopoeia and the International Organization for Standardization (ISO) 10993. A single 50 ml/kg body weight dose of the material was injected into mice by the intravenous route. The animals were observed at timed intervals for 7 days without any evidence of systemic toxicity.

Cytotoxicity was assessed using an in vitro biocompatibility study based on ISO 10993. A solution was prepared supplemented with 5% serum and 2% antibiotics, placed over confluent monolayers of L-929 mouse fibroblast cells propagated in 5% $CO_2$, and incubated at 37° C. in the presence of 5% $CO_2$ for 48 hours. The monolayers were examined microscopically at 48 hours and showed no evidence of a change in cell morphology, cell lysis, or cell toxicity.

The composition was also tested in vitro to see if it would cause hemolysis (lysis of red blood cells) when in contact with human red blood cells. The material was incubated in a solution of human red blood cells for 4 hours. After incubation, no released hemoglobin was detected, which indicated an absence of hemolysis.

The potential carcinogenicity of the composition was ascertained using a bacterial reverse mutation study in which mutagenic potential was assessed in histidine-dependent strains of bacteria. The genetically altered S. typhimurium strains TA98, TA100, TA1535, and TA1537 cannot grow in the absence of histidine unless specific mutations occur. The presence of mutagens increases the rates of these mutations. With the addition of 5 mg of the material per bacterial culture plate, there was no evidence of cytotoxicity or mutagenicity.

Further evaluation of potential carcinogenicity was performed by in vitro testing of chromosomal aberration in mammalian cell culture. The assay used Chinese hamster ovary cells to detect changes in chromosomal structure. The chromosomes were observed in metaphase which had been stained with Giemsa stain. No evidence of chromosomal aberration was detected.

Example 4

Hydroxyapatite Bone Filler Synthesis

A preferred composition blended with hydroxyapatite particles with utility as a bone filler may be produced in the following manner: A ratio of one part by weight of PLURONIC® F68NF (poloxamer 188) and two parts by weight of 22K random AOC (PLURACOL® V-10) are sealed in a heat-resistant glass container and heated to a temperature of 80° C. in an oven. The contents of the flask is stirred for a period of 8 hours at 80° C. A ratio of two parts by volume of the liquid polymer is blended with three parts of hydroxyapatite particles ranging in size from 50 to 300 microns, The composition is maintained at under a vacuum another 16 hours at 80° C. to allow air bubbles to escape from within the formulation. The composition is then dispensed directly into 1 cc syringes and cooled to a temperature of 4° C. After 15 minutes at 4° C., the syringes are placed into individual foil packets lined with a polyethylene coating. The product is sterilized using an appropriate dose of plasma radiation.

Example 5

Polyethylene Bone Filler Synthesis

A preferred composition blended with high density polyethylene particles with utility as a bone filler may be produced in the following manner: A ratio of one part by weight of F68NF (poloxamer 188) and two parts by weight of 22K random AOC are sealed in a heat-resistant glass container and heated to a temperature of 80° C. in an oven. The contents of the flask are stirred for a period of 8 hours at 80° C. The liquid polymer is then blended with an equal mass of high-density polyethylene particles ranging in size from 50 to 300 microns. The composition is maintained under reduced pressure for another 16 hours at 80° C. to allow air bubbles to escape from within the formulation. The composition is then dispensed directly into 1 cc syringes and cooled to a temperature of 4° C. After 15 minutes at 4° C., the syringes are placed into individual foil packets lined with a polyethylene coating. The product is sterilized by irradiation.

Example 6

Demineralized Bone Matrix Delivery

Under sterile conditions, demineralized bone matrix (DBM) particles (200 to 500 microns in size) were prepared. DBM was blended with the composition (2:3) so that each gram of the blend would contain 5 mg of DBM. A control of DBM blended in a 5% gelatin solution was used. Subclones of mouse myoblast cells were used to determine the bone making (osteogenesis) potential of the blends. This was achieved by assaying the alkylene phosphatase activity of the cells. The amount of osteogenic activity, as measured by alkaline phosphatase activity, was the same in both groups. The results of this study suggest that the composition is a suitable excipient for DBM.

Example 7

Formulation for Drug Delivery

The hydrophobic red dye Sudan IV was chosen as a surrogate for hydrophobic pharmaceutical agents. This dye is widely used as a lipid stain. It was combined with two different block AOC/random AOC composition, together with appropriate controls, in order to evaluate the ability of the composition to disperse the hydrophobic dye into an aqueous environment.

Dye was blended with the composition in two different ways: (1) Melt: the composition was heated to 80° C., 5 mg of dye per gram of wax was added and the molten mixture stirred until the dye was fully dissolved. The wax was then allowed to cool to room temperature. (2) Mix: because some drugs may be thermally labile, the dye (5 mg/g) and wax were kneaded together at room temperature until they gave a uniformly colored wax. The waxes evaluated were: (A) a 1:1 blend of poloxamer 188 and 22K random AOC; (B) a 1:1 blend of poloxamer 407 and 22K random AOC; (C) pure 22K random AOC. Controls were (D) beeswax and (E) Brij 700 (a PEO-stearate surfactant not suitable for parenteral use). The dye (5 mg/g) was added to (C), (D) and (E) by melting, as described above. 0.25 g of either A or B was added to 40 ml deionized water and allowed to dissolve completely, after which 12.5 mg of dye was added to these two beakers (A0 and B0) and to a third beaker (F0) containing 40 ml of deionised water. Immediately afterwards, 0.25 g of each of A1, A2, B1, B2, C1, D1, and E1 was then added to 40 ml of deionized water in a 50 ml beaker. All of the beakers were then stirred gently for 2 hours. Taking a stronger red color to indicate a better release of the dye, the results ranked as follows:

E1: Bright red solution with very few dye particles remaining.
B1: Red solution with a few dye particles remaining.
A1: Deep pink solution with a few dye particles remaining.
B2: Dirty red solution with dye particles remaining in suspension.
A2: Dirty pink solution with dye particles remaining in suspension.
C1: Pale red solution with dye particles in suspension.
B0: Very pale green solution with dye particles at the bottom of the flask.
A0: Very pale green solution with dye particles loosely aggregating at the air/water interface.
F0: Extremely pale green solution, tightly aggregated dye particles at the air/water interface.
D1: Clear solution with the floating colored wax showing no change.

The dye was almost completely insoluble in water or solutions of either A or B, and was not released from the beeswax, but was dispersed readily into solution when fully incorporated into either composition to an extent approaching that of Brij 700, a strong and non-biocompatible surfactant. A significant proportion of the dye was also dispersed after mechanical mixing of the solid dye (coarse powder/crystalline form). These results clearly illustrate the ability of biocompatible compositions to effectively release a hydrophobic material from an anhydrous form into an aqueous environment.

Other bioactive agents (e.g., carbohydrates, lipids, natural products and synthetic analogs thereof, nucleic acids, small molecules synthesized by man, proteins, antibiotics, antibodies, antigens, chemotherapeutics, imaging and contrast agents, radiotherapeutics, receptors or their ligands) may be used. The depot effects, if any, of the composition may also be assayed to determine whether there is any enhancement of biological activity.

Example 8

Water-Soluble Crayon

A preferred composition was blended with a dye to formulate a water-soluble crayon in the following manner: A ratio of three parts by weight of poloxamer 338 and one part by weight of PLURACOL® V-10 was sealed in a heat-resistant glass container and heated to a temperature of 80° C. in an oven. Dye was added at a concentration of 5 mg per gram of polymer and stirred until it dissolved. The liquid composition was then allowed to remain undisturbed for 16 hours at 80° C. to allow air bubbles to escape from within the liquid. The crayon was formed by pouring the liquid composition into molds and cooling to 4° C. for 15 minutes.

Example 9

Biocompatible Cleanser

The usefulness of the composition as a detergent may be assessed. Its surfactant activity and ability to remove stains or contaminants from the surface of a device or instrument can be compared to other detergents used in clinical settings. Viscous compositions may be used in situations where the cleanser is intended to adhere to the surface in need of deep cleansing; otherwise, non-viscous compositions may be used for quick washing and rinsing. The biocompatibility of the compositions would be advantageous because of the ease with which the cleaned device or instrument re-enters use in the clinic. This is an alternative to harsh detergent cleansers.

Example 10

Non-Corrosive Lubricant

The usefulness of the composition as a lubricant may be assessed. Its ability to make a medical device, surgical implant, or instrument slippery can be compared to other lubricants used in clinical settings. Compositions of varying viscosity (e.g., oil to grease) may be used depending on the situation. The biocompatibility of composition and its rapid elimination would be advantageous because of its safety.

Patents, patent applications, books, and other publications cited herein are incorporated by reference in their entirety.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

TABLE 1A

| COMPOSITION | | | | APPEARANCE | | | Polymer |
|---|---|---|---|---|---|---|---|
| Random AOC | % | Block AOC or AOH | % | Light Adsorbance | | Surface Texture | Compatibility |
| 22K | 98 | F68 | 2 | 1 | very clear | 1 very smooth | Good |
| 22K | 95 | F68 | 5 | 1 | very clear | 1 very smooth | Good |
| 22K | 90 | F68 | 10 | 1 | very clear | 1 very smooth | Good |
| 22K | 80 | F68 | 20 | 1 | very clear | 1 very smooth | Good |
| 22K | 70 | F68 | 30 | 1 | very clear | 2 smooth | Good |
| 22K | 60 | F68 | 40 | 1.5 | clear to very clear | 3 textured | Good |
| 22K | 50 | F68 | 50 | 2 | clear | 3 textured | Good |
| 22K | 40 | F68 | 60 | 3 | semi-clear | 4 cobblestone | Good |
| 22K | 30 | F68 | 70 | 5 | white opaque | 5 coarse | Good |
| 22K | 20 | F68 | 80 | 6 | white opaque | 4 cobblestone | Good |
| 22K | 10 | F68 | 90 | 6 | white opaque | 4 cobblestone | Good |
| 22K | 5 | F68 | 95 | 7 | white opaque | 4 cobblestone | Good |
| 22K | 2 | F68 | 98 | 7 | white opaque | 4 cobblestone | Good |
| 22K | 50 | F88 | 50 | 3 | semi-clear | 1 very smooth | Good |
| 22K | 70 | F98 | 30 | 1 | very clear | 4 cobblestone | Good |
| 22K | 60 | F98 | 40 | 2 | clear | 4 cobblestone | Good |
| 22K | 50 | F98 | 50 | 2 | clear | 4 cobblestone | Good |
| 22K | 50 | F108 | 50 | 5 | white opaque | 4 cobblestone | Good |
| 22K | 25 | F108 | 75 | 5 | white opaque | 4 smooth to coarse | Good |
| 22K | 50 | F87 | 50 | 2 | clear | 2 smooth | Good |
| 22K | 50 | F127 | 50 | 6 | white opaque | 4 cobblestone | Good |
| 22K | 50 | PEO 1.5K | 50 | 3 | semi-clear | 2 smooth | Good |
| 22K | 50 | PEO 2.0K | 50 | 2.5 | semi-clear, clear (edge) | 4 cobblestone | Good |
| 22K | 80 | PEO 3.5K | 20 | 2 | clear | 3 textured | Good |
| 22K | 70 | PEO 3.5K | 30 | 2 | clear | 3 textured | Good |
| 22K | 60 | PEO 3.5K | 40 | 2.5 | semi-clear, clear | 4 cobblestone | Good |
| 22K | 50 | PEO 3.5K | 50 | 4 | mottled white/clear | 5 coarse | Good |
| 22K | 40 | PEO 3.5K | 60 | 4 | mottled white/clear | 5 coarse | Good |
| 22K | 30 | PEO 3.5K | 70 | 4 | mottled white/clear | 5 coarse | Good |

TABLE 1A-continued

| COMPOSITION | | | | APPEARANCE | | | | Polymer Compatibility |
|---|---|---|---|---|---|---|---|---|
| Random AOC | % | Block AOC or AOH | % | Light Adsorbance | | Surface Texture | | |
| 22K | 20 | PEO 3.5K | 80 | 5 | white | 4 | cobblestone | Good |
| 22K | 50 | PEO 5.0K | 50 | 2.5 | semi-clear, clear patches | 4 | cobblestone | Good |
| 22K | 50 | PEO 7.5K | 50 | 6 | white opaque | 4 | cobblestone | Partial |
| 22K | 50 | PEO 12K | 50 | 6 | white opaque | 4 | cobblestone | Incompatible |

TABLE 2A

| COMPOSITION | | | | APPEARANCE | | | | Polymer Compatibility |
|---|---|---|---|---|---|---|---|---|
| Random AOC | % | Block AOC or AOH | % | Light Adsorbance | | Surface Texture | | |
| 12K | 50 | F68 | 50 | 2 | very clear | 4 | cobblestone | Good |
| 12K | 50 | F88 | 50 | 4 | very clear to white (edge) | 2 | smooth | Good |
| 12K | 40 | F98 | 60 | 4 | mottled white/clear | 4 | cobblestone | Good |
| 12K | 75 | F108 | 25 | 1 | very clear | 3 | textured | Good |
| 12K | 50 | F108 | 50 | 3 | semi-clear | 4 | cobblestone | Good |
| 12K | 25 | F108 | 75 | 4 | mottled white/clear | 4 | cobblestone | Good |
| 12K | 50 | F127 | 50 | 6 | white opaque | 4 | cobblestone | Good |
| 12K | 50 | PEO 2.0K | 50 | 4 | semi-clear, clear (edge) | 4 | cobblestone | Good |
| 12K | 50 | PEO 3.5K | 50 | 4 | white, semi-clear (edge) | 3 | textured | Good |
| 12K | 50 | PEO 5.0K | 50 | 4 | mottled white/clear | 4 | cobblestone | Good |
| 12K | 50 | PEO 7.5K | 50 | 6 | white opaque | 4 | cobblestone | Partial |
| 12K | 50 | PEO 12K | 50 | 6 | white opaque | 4 | cobblestone | Incompatible |
| 12K | 50 | PEO 20K | 50 | 7 | bright white | 4 | cobblestone | Incompatible |
| 12K | 50 | PEO 35K | 50 | 7 | bright white | 4 | cobblestone | Incompatible |
| 3.9K | 50 | F68 | 50 | 7 | bright white | 3 | textured | Incompatible |
| 3.9K | 50 | F127 | 50 | 7 | bright white | 5 | coarse | Incompatible |
| 3.9K | 50 | PEO 1.5K | 50 | 7 | bright white | 3 | textured | Incompatible |
| 3.9K | 50 | PEO 2.0K | 50 | 7 | bright white | 3 | textured | Incompatible |
| 3.9K | 50 | PEO 3.5K | 50 | 7 | bright white | 3 | textured | Incompatible |
| 3.9K | 50 | PEO 5.0K | 50 | 7 | bright white | 3 | textured | Incompatible |
| 3.9K | 50 | PEO 7.5K | 50 | 5 | white | 0 | (liquid paste) | Incompatible |
| 3.9K | 50 | PEO 12K | 50 | 5 | white | 0 | (liquid paste) | Incompatible |

TABLE 1B

| COMPOSITIONS | | | | INITIAL PROPERTIES | | | | | |
|---|---|---|---|---|---|---|---|---|---|
| Random AOC | % | Block AOC or AOH | % | Hardness | | Plasticity | | Bulk Texture | |
| 22K | 98 | F68 | 2 | 1 | grease | 5 | plastic flow | 2 | homogeneous |
| 22K | 95 | F68 | 5 | 2 | semi-solid | 5 | plastic flow | 2 | homogeneous |
| 22K | 90 | F68 | 10 | 3 | very soft | 4 | bends, tears | 2 | homogeneous |
| 22K | 80 | F68 | 20 | 4 | soft | 4 | bends, tears | 2 | homogeneous |
| 22K | 70 | F68 | 30 | 4 | soft | 4 | bends, tears | 2 | homogeneous; |
| 22K | 60 | F68 | 40 | 5 | medium-soft | 3 | bends, breaks | 2 | homogeneous |
| 22K | 50 | F68 | 50 | 6 | medium | 3 | bends, breaks | 2 | homogeneous |
| 22K | 40 | F68 | 60 | 6 | medium | 3 | bends, breaks | 2 | homogeneous |
| 22K | 30 | F68 | 70 | 7 | medium-hard | 2 | snaps | 2 | homogeneous |
| 22K | 20 | F68 | 80 | 8 | hard | 2 | snaps | 2 | homogeneous |
| 22K | 10 | F68 | 90 | 9 | very hard | 1 | brittle | 2 | homogeneous |
| 22K | 5 | F68 | 95 | 9 | very hard | 1 | brittle | 2 | homogeneous |
| 22K | 2 | F68 | 98 | 10 | rock hard | 1 | brittle | 2 | homogeneous |
| 22K | 50 | F88 | 50 | 6 | medium | 3 | bends, breaks | 2 | homogeneous |
| 22K | 70 | F98 | 30 | 6 | medium | 3 | bends, breaks | 2 | homogeneous |
| 22K | 60 | F98 | 40 | 6 | medium | 3 | bends, breaks | 2 | homogeneous |
| 22K | 50 | F98 | 50 | 7 | medium-hard | 2 | snaps | 2 | homogeneous |
| 22K | 50 | F108 | 50 | 6 | medium | 3 | bends, breaks | 2 | homogeneous |
| 22K | 25 | F108 | 75 | 9 | very hard | 1 | brittle | 2 | homogeneous |
| 22K | 50 | F87 | 50 | 4 | soft | 4 | bends, tears | 2 | homogeneous |
| 22K | 50 | F127 | 50 | 4 | soft | 4 | bends, tears | 2 | homogeneous |
| 22K | 50 | PEO 1.5K | 50 | 4 | soft | 4 | bends, tears | 2 | homogeneous |
| 22K | 50 | PEO 2.0K | 50 | 5 | medium-soft | 3 | bends, breaks | 2 | homogeneous |
| 22K | 80 | PEO 3.5K | 20 | 3 | very soft | 4 | bends, tears | 2 | homogeneous |
| 22K | 70 | PEO 3.5K | 30 | 4 | soft | 4 | bends, tears | 2 | homogeneous |
| 22K | 60 | PEO 3.5K | 40 | 4 | soft | 4 | bends, tears | 2 | homogeneous |
| 22K | 50 | PEO 3.5K | 50 | 5 | medium-soft | 3 | bends, breaks | 2 | homogeneous |
| 22K | 40 | PEO 3.5K | 60 | 5 | medium-soft | 3 | bends, breaks | 2 | homogeneous |
| 22K | 30 | PEO 3.5K | 70 | 7 | medium-hard | 2 | snaps | 2 | homogeneous |
| 22K | 20 | PEO 3.5K | 80 | 8 | hard | 2 | snaps | 2 | homogeneous |

TABLE 1B-continued

| COMPOSITIONS | | | | INITIAL PROPERTIES | | | | | |
|---|---|---|---|---|---|---|---|---|---|
| Random AOC | % | Block AOC or AOH | % | Hardness | | Plasticity | | Bulk Texture | |
| 22K | 50 | PEO 5.0K | 50 | 7 | medium-hard | 3 | bends, breaks | 2 | homogeneous |
| 22K | 50 | PEO 7.5K | 50 | 5 | medium-soft | 4 | bends, tears | 2 | homogeneous |
| 22K | 50 | PEO 12K | 50 | 9 | very hard | 1 | brittle | 1 | small grains |

TABLE 2B

| COMPOSITION | | | | INITIAL PROPERTIES | | | | | |
|---|---|---|---|---|---|---|---|---|---|
| Random AOC | % | Block AOC or AOH | % | Hardness | | Plasticity | | Bulk Texture | |
| 12K | 50 | F68 | 50 | 7 | medium-hard | 3 | bends, breaks | 2 | homogeneous |
| 12K | 50 | F88 | 50 | 7 | medium-hard | 3 | bends, breaks | 2 | homogeneous |
| 12K | 40 | F98 | 60 | 8 | hard | 2 | snaps | 1 | small grains |
| 12K | 75 | F108 | 25 | 4 | soft | 4 | bends, tears | 2 | homogeneous |
| 12K | 50 | F108 | 50 | 7 | medium-hard | 3 | bends, breaks | 2 | homogeneous |
| 12K | 25 | F108 | 75 | 8 | hard | 2 | snaps | 1 | small grains |
| 12K | 50 | F127 | 50 | 4 | soft | 4 | bends, tears | 2 | homogeneous |
| 12K | 50 | PEO 2.0K | 50 | 4 | soft | 4 | bends, tears | 2 | homogeneous |
| 12K | 50 | PEO 3.5K | 50 | 4 | soft | 4 | bends, tears | 2 | homogeneous |
| 12K | 50 | PEO 5.0K | 50 | 7 | medium-hard | 3 | bends, breaks | 2 | homogeneous |
| 12K | 50 | PEO 7.5K | 50 | 6 | medium | 3 | bends, breaks | 2 | homogeneous |
| 12K | 50 | PEO 12K | 50 | 6 | medium | 3 | bends, breaks | 1 | small grains |
| 12K | 50 | PEO 20K | 50 | 6 | medium | 3 | bends, breaks | 1 | small grains |
| 12K | 50 | PEO 35K | 50 | 6 | medium | 3 | bends, breaks | 0 | large grains |
| 3.9K | 50 | F68 | 50 | 7 | medium-hard | 2 | snaps | 1 | small grains |
| 3.9K | 50 | F127 | 50 | 4 | soft | 1 | brittle | 1 | small grains |
| 3.9K | 50 | PEO 1.5K | 50 | 3 | very soft | 5 | (paste) | 1 | small grains |
| 3.9K | 50 | PEO 2.0K | 50 | 8 | hard | 2 | snaps | 1 | small grains |
| 3.9K | 50 | PEO 3.5K | 50 | 8 | hard | 2 | snaps | 1 | small grains |
| 3.9K | 50 | PEO 5.0K | 50 | 3 | very soft | 5 | (paste) | 1 | small grains |
| 3.9K | 50 | PEO 7.5K | 50 | 3 | very soft | 5 | (paste) | 1 | small grains |
| 3.9K | 50 | PEO 12K | 50 | 3 | very soft | 5 | (paste) | 0 | large grains |

TABLE 1C

| COMPOSITION | | | | PROPERTIES ON WORKING | | | | |
|---|---|---|---|---|---|---|---|---|
| Random AOC | % | Block AOC or AOH | % | Hardness | Ductility | Malleability | Cohesion | Adhesion |
| 22K | 98 | F68 | 2 | 0.5 | | | | 5 |
| 22K | 95 | F68 | 5 | 2 | | | | 5 |
| 22K | 90 | F68 | 10 | 2 | 3 | 4 | −2 | 6 |
| 22K | 80 | F68 | 20 | 3 | 3 | 4 | −1 | 5 |
| 22K | 70 | F68 | 30 | 3 | 3 | 3 | 0 | 4 |
| 22K | 60 | F68 | 40 | 4 | 3 | 3 | 0 | 2 |
| 22K | 50 | F68 | 50 | 5 | 3 | 2 | 0 | 1 |
| 22K | 40 | F68 | 60 | 5 | 2 | 2 | 0 | 0 |
| 22K | 30 | F68 | 70 | 5 | 2 | 2 | 0 | 0 |
| 22K | 20 | F68 | 80 | 6 | 2 | 1 | 1 | 0 |
| 22K | 10 | F68 | 90 | 7.5 | 0 | 0 | 2 | 0 |
| 22K | 5 | F68 | 95 | 9 | 0 | 0 | 2 | 0 |
| 22K | 2 | F68 | 98 | 9 | 0 | 0 | 2 | 0 |
| 22K | 50 | F88 | 50 | 10 | 2 | 2 | 0 | 0 |
| 22K | 70 | F98 | 30 | 5 | 3 | 3 | 0 | 2 |
| 22K | 60 | F98 | 40 | 4 | 3 | 2 | 0 | 1 |
| 22K | 50 | F98 | 50 | 5 | 2 | 2 | 0 | 1 |
| 22K | 50 | F108 | 50 | 5 | 3 | 2 | 0 | 0 |
| 22K | 25 | F108 | 75 | 4 | 3 | 0 | 0 | 0 |
| 22K | 50 | F87 | 50 | 9 | 3 | 4 | −2 | 5 |
| 22K | 50 | F127 | 50 | 2 | 3 | 3 | 0 | 2 |
| 22K | 50 | PEO 1.5K | 50 | 3.5 | 3 | 3 | 0 | 2 |
| 22K | 50 | PEO 2.0K | 50 | 4 | 3 | 3 | 0 | 1 |
| 22K | 80 | PEO 3.5K | 20 | 4.5 | 4 | 4 | −1 | 5 |
| 22K | 70 | PEO 3.5K | 30 | 2.5 | 4 | 4 | −1 | 5 |
| 22K | 60 | PEO 3.5K | 40 | 3.5 | 4 | 3 | 0 | 2 |
| 22K | 50 | PEO 3.5K | 50 | 4 | 4 | 3 | 0 | 1 |
| 22K | 40 | PEO 3.5K | 60 | 5 | 2 | 3 | 0 | 0 |
| 22K | 30 | PEO 3.5K | 70 | 6 | 2 | 2 | 0 | 0 |

TABLE 2C

| COMPOSITION | | | | PROPERTIES ON WORKING | | | | |
|---|---|---|---|---|---|---|---|---|
| Random AOC | % | Block AOC or AOH | % | Hardness | Ductility | Malleability | Cohesion | Adhesion |
| 22K | 20 | PEO 3.5K | 80 | 7 | 1 | 1 | 1 | 0 |
| 22K | 50 | PEO 5.0K | 50 | 3 | 3 | 3 | −1 | 3 |
| 22K | 50 | PEO 7.5K | 50 | 3 | 3 | 4 | −2 | 5 |
| 22K | 50 | PEO 12K | 50 | 9 | 1 | 0 | 2 | 0 |
| 12K | 50 | F68 | 50 | 2 | 3 | 2 | 0 | 2 |
| 12K | 50 | F88 | 50 | 2 | 3 | 2 | 0 | 1 |
| 12K | 40 | F98 | 60 | 0 | 1 | 0 | 2 | 0 |
| 12K | 75 | F108 | 25 | 4 | 3 | 4 | 0 | 4 |
| 12K | 50 | F108 | 50 | 2 | 3 | 2 | 0 | 3 |
| 12K | 25 | F108 | 75 | 0 | 1 | 0 | 2 | 0 |
| 12K | 50 | F127 | 50 | 4 | 3 | 4 | 0 | 3 |
| 12K | 50 | PEO 2.0K | 50 | 4 | 3 | 4 | −1 | 6 |
| 12K | 50 | PEO 3.5K | 50 | 4 | 3 | 4 | −1 | 6 |
| 12K | 50 | PEO 5.0K | 50 | 4 | 3 | 4 | 0 | 3 |
| 12K | 50 | PEO 7.5K | 50 | 2 | 3 | 2 | −1 | 5 |
| 12K | 50 | PEO 12K | 50 | | | | −3 | 4 |
| 12K | 50 | PEO 20K | 50 | | | | −3 | 4 |
| 12K | 50 | PEO 35K | 50 | | | | −3 | 4 |
| 3.9K | 50 | F68 | 50 | 0 | | | −3 | |
| 3.9K | 50 | F127 | 50 | 0 | | | −3 | 3 |
| 3.9K | 50 | PEO 1.5K | 50 | | | | −3 | |
| 3.9K | 50 | PEO 2.0K | 50 | 0 | | | −3 | |
| 3.9K | 50 | PEO 3.5K | 50 | 0 | | | −3 | |
| 3.9K | 50 | PEO 5.0K | 50 | | | | −3 | |
| 3.9K | 50 | PEO 7.5K | 50 | | | | −3 | |
| 3.9K | 50 | PEO 12K | 50 | | | | −3 | |

Hardness: 1 = grease, 2 = semi-solid, 3 = very soft, 4 = soft, 5 = medium soft, 6 = medium, 7 = medium-hard, 8 = hard, 9 = very hard, 10 = rock hard
Ductility: 0 = crumbles, 1 and 2 = fractures, 3 = does not fracture, 4 = stretchable
Malleability: 0 = not deformable, 1 = poorly moldable, 2 = moldable with work, 3 = readily moldable, 4 = very moldable
Adhesion: 0 = non-tacky, 1 = slight tack, 2 = tacky, 3 = very tacky, 4 = moderately sticky, 5 = sticky, 6 = very sticky
Cohesion: −2 = cohesion, −1 = soft/reduced cohesion, 0 = cohesive, 1 = hard/barely cohesive, 2 = crumbles

What is claimed is:

1. A composition consisting of: (i) solid or porous particles; (ii) a random copolymer having a molecular mass of at least 5 kg/mol, and comprising ethylene oxide and one or more other alkylene oxide(s); and (iii) a non-random polymer comprising one or more alkylene oxide(s).

2. The composition of claim 1, wherein said composition can adhere to body tissue.

3. The composition of claim 1, wherein said composition is biocompatible and substantially non-toxic.

4. The composition of claim 1, wherein the random copolymer and the non-random polymer are substantially non-metabolizable and readily eliminated in unmodified form.

5. The composition of claim 1, wherein said composition is substantially anhydrous.

6. The composition of claim 1, wherein said composition has a consistency at 25° C. of a viscous oil to a hard wax.

7. The composition of claim 1, wherein said random copolymer has a molecular mass of at least 10 kg/mol.

8. The composition of claim 1, wherein said random copolymer has a molecular mass of at least 20 kg/mol.

9. The composition of claim 1, wherein said random copolymer has a molecular mass of not more than 25 kg/mol.

10. The composition of claim 1, wherein said random copolymer has a molecular mass of not more than 50 kg/mol.

11. The composition of claim 1, wherein said random copolymer has a molecular mass of not more than 200 kg/mol.

12. The composition of claim 1, wherein said random copolymer has a molecular mass from 1 kg/mol to 1000 kg/mol.

13. The composition of claim 1, wherein said other alkylene oxide(s) is propylene oxide and/or butylene oxide.

14. The composition of claim 1, wherein said other alkylene oxide is propylene oxide, and said random copolymer has (i) a molecular mass from 15 kg/mol to 30 kg/mol and (ii) a mass ratio of the ethylene oxide to the propylene oxide from 25:75 to 75:25.

15. The composition of claim 14, wherein said random copolymer has a molecular mass from 20 kg/mol to 25 kg/mol.

16. The composition of claim 14, wherein said random copolymer has a mass ratio of the ethylene oxide to the propylene oxide from 40:60 to 60:40.

17. The composition of claim 1, wherein said non-random polymer of alkylene oxide(s) is a homopolymer.

18. The composition of claim 17, wherein said homopolymer has a molecular mass from 1 kg/mol to 20 kg/mol.

19. The composition of claim 17, wherein said homopolymer has a molecular mass from 1 kg/mol to 10 kg/mol.

20. The composition of claim 17, wherein said homopolymer is poly(ethylene oxide).

21. The composition of claim 1, wherein said non-random polymer is selected from the group consisting of poloxamer, meroxapol, poloxamine, and reverse poloxamine.

22. The composition of claim 1, wherein said non-random polymer is a block copolymer.

23. The composition of claim 22, wherein said block copolymer is a poloxamer selected from the group consisting of poloxamer 108, poloxamer 188, poloxamer 238, poloxamer 288, poloxamer 338, poloxamer 235, poloxamer 237, poloxamer 335, and poloxamer 407.

24. The composition of claim 22, wherein said block copolymer is a copolymer of ethylene oxide and propylene oxide.

25. The composition of claim 24, wherein said block copolymer has a molecular mass from 10 kg/mol to 50 kg/mol.

26. The composition of claim 24, wherein said block copolymer has a mass ratio of the ethylene oxide to the propylene oxide from 25:75 to 95:5.

27. The composition of claim 22, wherein said block copolymer is a triblock copolymer of ethylene oxide and propylene oxide.

28. The composition of claim 27, wherein said triblock copolymer has a molecular mass from 4 kg/mol to 20 kg/mol.

29. The composition of claim 28, wherein said triblock copolymer has a mass ratio of the ethylene oxide to the propylene oxide from 25:75 to 95:5.

30. The composition of claim 24, wherein said block copolymer has (i) a molecular mass from 6 kg/mol to 10 kg/mol and (ii) a mass ratio of the ethylene oxide to the propylene oxide from 60:40 to 90:10.

31. The composition of claim 24, wherein said block copolymer has (i) a molecular mass from 10 kg/mol to 15 kg/mol and (ii) a mass ratio of the ethylene oxide to the propylene oxide from 60:40 to 90:10.

32. The composition of claim 1, wherein said particles are from 10% by volume to 64% by volume.

33. The composition of claim 1, wherein said particles have a size from 35 microns to 500 microns.

34. The composition of claim 1, wherein said particles are selected from the group consisting of bone chips or powder, demineralized bone, hydroxyapatite, polyethylene, and any combination thereof.

35. A method of using the composition of claim 1, which comprises administering said composition to a subject.

36. A process of making a product useful for medicine or surgery, which comprises suspending (a) solid or porous particles in (b) a carrier consisting of (i) at least one random copolymer having a molecular mass of at least 5 kg/mol, and comprising ethylene oxide and one or more other alkylene oxide(s) and (ii) at least one non-random polymer comprising one or more alkylene oxide(s).

* * * * *